United States Patent
Koh et al.

(10) Patent No.: US 10,981,174 B1
(45) Date of Patent: Apr. 20, 2021

(54) PROTEIN AND NUCLEIC ACID DETECTION FOR MICROFLUIDIC DEVICES

(71) Applicant: National Technology & Engineering Solutions of Sandia, LLC, Albuquerque, NM (US)

(72) Inventors: Chung-Yan Koh, Dublin, CA (US); Christopher Phaneuf, Rancho Mirage, CA (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 119 days.

(21) Appl. No.: 16/399,484

(22) Filed: Apr. 30, 2019

Related U.S. Application Data

(63) Continuation-in-part of application No. 15/669,426, filed on Aug. 4, 2017, now Pat. No. 10,406,528.

(60) Provisional application No. 62/370,843, filed on Aug. 4, 2016.

(51) Int. Cl.
| | | |
|---|---|---|
| *B01L 7/00* | (2006.01) | |
| *C12Q 1/68* | (2018.01) | |
| *C12Q 1/6844* | (2018.01) | |
| *B01L 3/00* | (2006.01) | |

(52) U.S. Cl.
CPC ............ *B01L 7/525* (2013.01); *C12Q 1/6844* (2013.01); *B01L 2300/0803* (2013.01); *B01L 2300/168* (2013.01); *B01L 2300/1872* (2013.01); *B01L 2300/1894* (2013.01)

(58) Field of Classification Search
CPC ............ B01L 7/525; B01L 2300/0803; B01L 2300/168; B01L 2300/1872; B01L 2300/1894; C12Q 1/6844
See application file for complete search history.

(56) References Cited

U.S. PATENT DOCUMENTS

| | | |
|---|---|---|
| 3,555,284 A | 1/1971 | Anderson |
| 3,744,974 A | 7/1973 | Maddox et al. |
| 4,125,375 A | 11/1978 | Hunter |
| 4,156,570 A | 5/1979 | Wardlaw |
| 4,554,071 A | 11/1985 | Ruijten et al. |
| 4,656,143 A | 4/1987 | Baker et al. |
| 4,683,579 A | 7/1987 | Wardlaw |
| 4,833,073 A | 5/1989 | McNally et al. |
| 4,844,818 A | 7/1989 | Smith |

(Continued)

FOREIGN PATENT DOCUMENTS

| | | | |
|---|---|---|---|
| WO | WO 2008/143578 A1 | 11/2008 | |
| WO | WO 2009/098237 A1 | 8/2009 | |
| WO | WO-2015175856 A1 * | 11/2015 | ........... C12Q 1/6844 |

OTHER PUBLICATIONS

U.S. Appl. No. 13/423,008, filed Mar. 16, 2012, Koh et al.

(Continued)

*Primary Examiner* — Jennifer Wecker
(74) *Attorney, Agent, or Firm* — Helen S. Baca

(57) ABSTRACT

The present invention relates to methods for detecting targets by employing a temperature control system with a microfluidic device. The system allows for non-contact heating by employing an infrared emitter. In some instances, the system can be used in conjunction with a centrifugal microfluidic device. Optionally, a mask can be implemented to provide selective heating of desired assay areas of the device.

20 Claims, 19 Drawing Sheets

(56) References Cited

U.S. PATENT DOCUMENTS

| | | |
|---|---|---|
| 5,279,936 A | 1/1994 | Vorpahl |
| 5,635,362 A | 6/1997 | Levine et al. |
| 5,639,428 A | 6/1997 | Cottingham |
| 5,705,628 A | 1/1998 | Hawkins |
| 5,882,903 A | 3/1999 | Andrevski et al. |
| 5,892,577 A | 4/1999 | Gordon |
| 6,153,148 A | 11/2000 | Thomas |
| 6,319,469 B1 | 11/2001 | Mian et al. |
| 6,503,722 B1 | 1/2003 | Valkirs |
| 6,887,384 B1 | 5/2005 | Frechet et al. |
| 6,960,449 B2 | 11/2005 | Wang et al. |
| 7,033,747 B2 | 4/2006 | Gordon |
| 7,157,049 B2 | 1/2007 | Valencia et al. |
| 7,312,085 B2 | 12/2007 | Chou et al. |
| 7,332,326 B1 | 2/2008 | Kellogg et al. |
| 7,749,772 B1 | 7/2010 | Wang |
| 7,758,810 B2 | 7/2010 | Lee et al. |
| 7,790,400 B2 | 9/2010 | Jehanli et al. |
| 8,337,775 B2 | 12/2012 | Pugia et al. |
| 8,945,914 B1 | 2/2015 | Schaff et al. |
| 8,962,346 B2 | 2/2015 | Schaff et al. |
| 9,186,668 B1 | 11/2015 | Schaff et al. |
| 9,244,065 B1 | 1/2016 | Schaff et al. |
| 9,304,128 B1 * | 4/2016 | Koh ................. G01N 33/5304 |
| 9,304,129 B2 | 4/2016 | Schaff et al. |
| 9,500,579 B1 | 11/2016 | Sommer et al. |
| 9,702,871 B1 | 7/2017 | Koh et al. |
| 9,766,230 B1 | 9/2017 | Koh et al. |
| 2001/0055812 A1 | 12/2001 | Mian et al. |
| 2002/0098535 A1 | 7/2002 | Wang et al. |
| 2002/0106786 A1 | 8/2002 | Carvalho et al. |
| 2002/0137068 A1 | 9/2002 | Haugland et al. |
| 2002/0151043 A1 | 10/2002 | Gordon |
| 2002/0153251 A1 | 10/2002 | Sassi et al. |
| 2002/0164659 A1 | 11/2002 | Rao et al. |
| 2002/0170825 A1 | 11/2002 | Lee et al. |
| 2003/0013203 A1 | 1/2003 | Jedrzejewski et al. |
| 2003/0078499 A1 | 4/2003 | Eppstein |
| 2003/0124719 A1 | 7/2003 | Woodside |
| 2003/0203504 A1 | 10/2003 | Hefti |
| 2004/0072278 A1 | 4/2004 | Chou et al. |
| 2005/0186685 A1 | 8/2005 | Kange et al. |
| 2005/0191682 A1 | 9/2005 | Barone et al. |
| 2005/0215410 A1 | 9/2005 | Merino et al. |
| 2005/0282220 A1 | 12/2005 | Prober et al. |
| 2006/0078955 A1 | 4/2006 | Lin et al. |
| 2006/0171654 A1 | 8/2006 | Hawkins et al. |
| 2008/0053194 A1 | 3/2008 | Ahmad |
| 2008/0108047 A1 | 5/2008 | Woodside |
| 2008/0149484 A1 | 6/2008 | Tolley et al. |
| 2009/0004059 A1 | 1/2009 | Pugia et al. |
| 2009/0069554 A1 | 3/2009 | Finne |
| 2009/0209402 A1 | 8/2009 | Andersson |
| 2009/0325186 A1 | 12/2009 | Hinnah et al. |
| 2010/0068754 A1 | 3/2010 | Kirakossian |
| 2010/0120596 A1 | 5/2010 | Froman et al. |
| 2010/0151560 A1 | 6/2010 | Wo et al. |
| 2010/0302539 A1 | 12/2010 | Myrick et al. |
| 2011/0045958 A1 | 2/2011 | Pedrazzini |
| 2013/0260447 A1 | 10/2013 | Link |
| 2014/0273241 A1 | 9/2014 | Ochranek et al. |
| 2015/0360225 A1 | 12/2015 | Schaff et al. |
| 2016/0061829 A1 | 3/2016 | Schaff et al. |
| 2016/0178619 A1 | 6/2016 | Koh et al. |
| 2018/0037932 A1 | 2/2018 | Koh et al. |
| 2018/0037960 A1 | 2/2018 | Koh et al. |
| 2018/0065118 A1 | 3/2018 | Koh et al. |

OTHER PUBLICATIONS

U.S. Appl. No. 13/941,186, filed Jul. 12, 2013, Koh et al.
U.S. Appl. No. 14/090,040, filed Nov. 26, 2013, Koh et al.
U.S. Appl. No. 14/957,405, filed Dec. 2, 2015, Koh.
U.S. Appl. No. 15/785,708, filed Oct. 17, 2017, Koh et al.

Abi-Samra et al., "Infrared controlled waxes for liquid handling and storage on a CD-microfluidic platform", Lab on a Chip, 2011, vol. 11, pp. 723-726.
Abi-Samra et al., "Electrochemical velocimetry on centrifugal microfluidic platforms", Lab on a Chip, 2013, vol. 13, pp. 3253-3260.
Ahanotu et al., "Staphylococcal enterotoxin B as a biological weapon: recognition, management, and surveillance of Staphylococcal enterotoxin", Applied Biosafety, 2006, vol. 11 (3), pp. 120-126.
Albrecht et al., "Micro free-flow IEF enhanced active cooling and functionalized gels", Electrophoresis, 2006, vol. 27, pp. 4960-4969.
Amasia et al., "Centrifugal microfluidic platform for rapid PCR amplification using integrated thermoelectric heating and ice-valving", Sensors and Actuators B, 2012, vol. 161, pp. 1191-1197.
Amersham Biosciences AB, "Percoll: Methodology and Applications", Handbook No. 18-1115-69 (Ed. AC), 2001, Uppsala, Sweden, pp. 1-84.
Amukele et al., "Ricin A-chain activity on stem-loop and unstructured DNA substrates", Biochemistry, 2005, vol. 44(11), pp. 4416-4425.
Andersson et al., "Parallel nanoliter microfluidic analysis system", Analytical Chemistry, 2007, vol. 79(11), pp. 4022-4030.
Baldwin, "How Hofmeister ion interactions affect protein stability", Biophysical Journal, 1996, vol. 71, pp. 2056-2063.
Ball et al., "Quenching of unincorporated amplification signal reporters in reverse-transcription loop-mediated isothermal amplification enabling bright, single-step, closed-tube, and multiplexed detection of RNA viruses", Analytical Chemistry, 2016, vol. 88, pp. 3562-3568.
Berlier et al., "Quantitative comparison of long-wavelength Alexa Fluor dyes to Cy dyes: fluorescence of the dyes and their bioconjugates", Journal of Histochemistry and Cytochemistry, 2003, vol. 51(12), pp. 1699-1712.
Berry et al., "One-step purification of nucleic acid for gene expression analysis via immiscible filtration assisted by surface tension", Lab on a Chip, 2011, vol. 11(10), pp. 1747-1753.
Boyko et al., "Cell-free DNA—a marker to predict ischemic brain damage in a rat stroke experimental model", Journal of Neurosurgery and Anesthesiology, 2011, vol. 23(3), pp. 222-228.
Brigotti et al., "Shiga toxin 1 acting on DNA in vitro is a heat-stable enzyme not requiring proteolytic activation", Biochimie Journal, 2004, vol. 86(45), pp. 305-309.
Buck et al., "Design strategies and performance of custom DNA sequencing primers", Biotechniques, 1999, vol. 27(3), pp. 528-536.
Cabrera et al., "Formation of natural pH gradients in a microfluidic device under flow conditions: model and experimental validation", Analytical Chemistry, 2001, vol. 73(3), pp. 658-666.
Carney, "Rapid diagnostic tests employing latex particles", Analytical Proceedings, 1990, vol. 27, pp. 99-100.
Chen et al., "Wirelessly adaptable heater array for centrifugal microfluidics and *Escherichia coli* sterilization", 35th Annual International Conference of the IEEE EMBS, held Jul. 3-7, 2013 in Osaka, Japan, pp. 5505-5508.
Churchill et al., "Detection of *Listeria monocytogenes* and the toxin listeriolysin O in food", Journal of Microbiological Methods, 2006, vol. 64(2), pp. 141-170.
Cui et al., "Multistage isoelectric focusing in a polymeric microfluidic chip", Analytical Chemistry, 2005, vol. 77(24), pp. 7878-7886.
Curtis et al., "A molecular approach to bioseparations: protein-protein and protein-salt interactions", Chemical Engineering Science, 2006, vol. 61, pp. 907-923.
Czeiger et al., "Measurement of circulating cell-free DNA levels by a new simple fluorescent test in patients with primary colorectal cancer", American Journal of Clinical Pathology, 2011, vol. 135(2), pp. 264-270.
Das et al., "Effects of separation length and voltage on isoelectric focusing in a plastic microfluidic device", Electrophoresis, 2006, vol. 27(18), pp. 3619-3626.
Endo et al., "RNA N-glycosidase activity of ricin A-chain. Mechanism of action of the toxic lectin ricin on eukaryotic ribosomes", The Journal of Biological Chemistry, 1987, vol. 262(17), pp. 8128-8130.

(56) References Cited

OTHER PUBLICATIONS

Fologea et al, "Detecting single stranded DNA with a solid state nanopore", Nano Letters, 2005, vol. 5(10), pp. 1905-1909.
Glorikian et al., "Microfluidics for IVDS—Smart consumable product development: implications for molecular diagnostics", DX Directions 2010, Spring, pp. 12-16.
Goldshtein et al., "A rapid direct fluorescent assay for cell-free DNA quantification in biological fluids", Annals of Clinical Biochemistry, 2009, vol. 46(Pt 6), pp. 488-494.
Gorkin et al., "Centrifugal microfluidics for biomedical applications", Lab on a Chip, 2010, vol. 10, pp. 1758-1773.
Gusev et al., "Capillary columns with in situ formed porous monolithic packing for micro high-performance liquid chromatography and capillary electrochromatography", Journal of Chromatography A, 1999, vol. 855(1), pp. 273-290.
Hatch et al., "Integrated preconcentration SDS-PAGE of proteins in microchips using photopatterned cross-linked polyacrylamide gels", Analytical Chemistry, 2006, vol. 78(14), pp. 4976-4984.
Heraeus, "Infrared emitters for industrial processes", Heraeus Noblelight GmbH brochure No. 0915 HNG-B 30 E 5C, pp. 1-16.
Heraeus, "New generation: short carbon infrared emitters", Heraeus Noblelight GmbH data sheet, Jan. 2015, 1 p.
Herr et al., "Microfluidic immunoassays as rapid saliva-based clinical diagnostics", Proceedings of the National Academy of Science USA, 2007, vol. 104(13), pp. 5268-5273.
Herr et al., "On-chip coupling of isoelectric focusing and free solution electrophoresis for multidimensional separations", Analytical Chemistry, 2003, vol. 75(5), pp. 1180-1187.
Holmberg et al., "Depurination of A4256 in 28 S rRNA by the ribosome-inactivating proteins from barley and ricin results in different ribosome conformations", Journal of Molecular Biology, 1996, vol. 259(1), pp. 81-94.
Holmes et al., "Leukocyte analysis and differentiation using high speed microfluidic single cell impedance cytometry", Lab on a Chip, 2009, vol. 9, pp. 2881-2889.
Huang et al., "The primary structure of Staphylococcal enterotoxin B: III. The cyanogen bromide peptides of reduced and aminoethylated enterotoxin B, and the complete amino acid sequence", Journal of Biological Chemistry, 1970, vol. 245(14), pp. 3518-3525.
Huang et al., "Microfabrication of a tapered channel for isoelectric focusing with thermally generated pH gradient", Electrophoresis, 2002, vol. 23(20), pp. 3504-3510.
IVD Technology, "Microfluidic applications for IVDs", DX Directions, 2010, Spring, pp. 6.
Kim et al., "Fully integrated lab-on-a-disc for nucleic acid analysis of food-borne pathogens", Analytical Chemistry, 2014, vol. 86, pp. 3841-3848.
Koh et al., "Centrifugal microfluidic platform for ultrasensitive detection of botulinum toxin", Analytical Chemistry, 2015, vol. 81, pp. 922-928.
Koh et al., "Centrifugal microfluidic platform for integrated analysis of proteins and nucleic acids from clinical and environmental samples", Sandia Report SAND2016-4449A, microTAS 2016, held on Oct. 9-13, 2016 in Dublin, Ireland (2 pp.).
Lauridsen et al., "Nucleic aptamers against biotoxins: a new paradigm toward the treatment and diagnostic approach", Nucleic Acid Therapeutics, 2012, vol. 22(6), pp. 371-379.
Lee et al., "Fully integrated lab-on-a-disc for simultaneous analysis of biochemistry and immunoassay from whole blood", Lab on a Chip, 2011, vol. 11(1), pp. 70-78.
Lee et al., "A fully automated immunoassay from whole blood on a disc", Lab on a Chip, 2009, vol. 9(11), pp. 1548-1555.
Lim et al., "Bead-based microfluidic immunoassays: The next generation", Biosensors and Bioelectronics, 2007, vol. 22(7), pp. 1197-1204.
Lim et al., "Rapid isoelectric trapping in a micropreparative-scale multicompartment electrolyzer", Electrophoresis, 2007, vol. 28(12), pp. 1851-1859.
Lo et al., "Photopolymerized diffusion-defined polyacrylamide gradient gels for on-chip protein sizing", Lab on a Chip, 2008, vol. 8(8), pp. 1273-1279.
Lo et al., "Plasma DNA as a prognostic marker in trauma patients", Clinical Chemistry, 2000, vol. 46(3), pp. 319-323.
Long et al., "Integration of nanoporous membranes for sample filtration/preconcentration in microchip electrophoresis", Electrophoresis, 2006, vol. 27(24), pp. 4927-4934.
Madou et al., "Lab on a CD", Annual Review of Biomedical Engineering, 2006, vol. 8, pp. 601-628.
Maes et al., "Comparison of sample fixation and the use of LDS-751 or anti-CD45 or leukocyte identification in mouse whole blood for flow cytometry", Journal of Immunological Methods, 2007, vol. 319(1-2), pp. 79-86.
Martinez-Duarte et al., "The integration of 3D carbon-electrode dielectrophoresis on a CD-like centrifugal microfluidic platform", Lab on a Chip, 2010, vol. 10, pp. 1030-1043.
McBain et al., "Polyethyleneimine functionalized iron oxide nanoparticles as agents for DNA delivery and transfection", Journal of Material Chemistry, 2007, vol. 17(24), pp. 2561-2565.
Melting Temperature Calculation. Retrieved on asf from the internet: http://www.biophp.org/minitools/melting_temperature/demo.php?primer=CGT+TAC+CCG+CAG&basic-1&NearestNeighbor=1&cp=200&cs=50&cmg=0.
Min et al., "Functional integration of DNA purification and concentration into a real time micro-PCR chip", Lab on a Chip, 2011, vol. 11(2), pp. 259-265.
Phaneuf et al., "Portable centrifugal microfluidic platform for nucleic acid detection", SAND Report SAND2016-4452A, 20th International Conference on Miniaturized Systems for Chemistry and Life Sciences, held on Oct. 9-13, 2016 in Dublin, Ireland, 2 pp.
Phaneuf et al., "Portable centrifugal microfluidic platform for nucleic acid detection", SAND Report SAND2016-7047C, 20th International Conference on Miniaturized Systems for Chemistry and Life Sciences, held on Oct. 9-13, 2016 in Dublin, Ireland, 2 pp.
Phaneuf et al., "Portable centrifugal microfluidic platform for nucleic acid detection", SAND Report SAND2016-10698C, 20th International Conference on Miniaturized Systems for Chemistry and Life Sciences, held on Oct. 9-13, 2016 in Dublin, Ireland, 1 p.
Phaneuf et al., "Non-contact heating system for a centrifugal microfluidic platform", SAND Report SAND2015-8608C, Proposed for presentation at the Lab-on-a-Chip, Microfluidics & Microarrays World Congress, held on Sep. 28-30, 2015 in San Diego, CA, 1 p.
Phaneuf et al., "Non-contact heating system for a centrifugal microfluidic platform", SAND Report SAND2015-3786A, 19th International Conference on Miniaturized Systems for Chemistry and Life Sciences, held on Oct. 25-29, 2015 in Gyeongju, South Korea, 2 pp.
Phaneuf et al., "Rapid, portable, multiplexed detection of bacterial pathogens directly from clinical sample matrices", Biosensors, 2016, vol. 6, article 49 (10 pp.).
Phaneuf et al., "Portable centrifugal microfluidic system for diagnostics in resource-limited settings", 2016 IEEE Healthcare Innovation Point-Of-Care Technologies Conference (HI-POCT), held on Nov. 9-11, 2016 in Cancun, Mexico, 3 pp.
Price et al., "Light-scattering immunoassay", in Principles and Practice Immunoassay (Second Ed., C.P. Price & D.J. Newman, eds.), 1997, Stockton Press (New York, NY), Chap. 18, pp. 446-481.
Rhodes et al., "Plasma DNA concentration as a predictor of mortality and sepsis in critically ill patients", Critical Care, 2006, vol. 10(2), Article R60 (pp. 1-7).
Riahi et al., "Molecular detection of bacterial pathogens using microparticle enhanced double-stranded DNA probes", Analytical Chemistry, 2011, vol. 83(16), pp. 6349-6354 and Supporting Information (8 pp.).
Rider et al., "A B cell-based sensor for rapid identification of pathogens", Science, 2003, vol. 301, pp. 213-215.
Riegger et al., "Read-out concepts for multiplexed bead-based fluorescence immunoassays on centrifugal microfluidic platforms", Sensors and Actuators A—Physical, 2006, vol. 126, pp. 455-462.

(56) References Cited

OTHER PUBLICATIONS

Roy et al., "From cellular lysis to microarray detection, an integrated thermoplastic elastomer (TPE) point of care lab on a disc", Lab on a Chip, 2015, vol. 15, pp. 406-416.

Saukkonen et al., "Cell-free plasma DNA as a predictor of outcome in severe sepsis and septic shock", Clinical Chemistry, 2008, vol. 54(6), pp. 1000-1007.

Schaff et al., "Differential white cell count by centrifugal microfluidics", microTAS 2010 Conference, held on Oct. 3-7, 2010 in Groningen, The Netherlands, 1 p.

Schaff et al., "Whole blood immunoassay based on centrifugal bead sedimentation", Clinical Chemistry, 2011, vol. 57(5), pp. 753-761.

Schembri et al., "Portable simultaneous multiple analyte whole-blood analyzer for point-of-care testing", Clinical Chemistry, 1992, vol. 38(9), pp. 1665-1670.

Schneider et al., "Characterization of EBV-Genome negative "null" and "t" cell lines derived from children with acute lymphoblastic leukemia and leukemic transformed non-Hodgkin lymphoma", International Journal of Cancer, 1977, vol. 19(5), pp. 621-626.

Sommer et al., "On-chip isoelectric focusing using photopolymerized immobilized pH gradients", Analytical Chemistry, 2008, vol. 80(9), pp. 3327-3333.

Suzuki et al., "Experimental optimization of probe length to increase the sequence specificity of high-density oligonucleotide microarrays", BMC Genomics, 2007, vol. 8, Art. 373 (13 pp.).

Tan et al., "Miniaturized capillary isoelectric focusing in plastic microfluidic devices", Electrophoresis, 2002, vol. 23(20), pp. 3638-3645.

Yu et al., "Bioinformatic processing to identify single nucleotide polymorphism that potentially affect Ape1 function", Mutation Research/Genetic Toxicology and Environmental Mutagenesis, 2011, vol. 722(2), pp. 140-146.

Zhang et al., "A new biodosimetric method: branched DNA-based quantitative detection of B1 DNA in mouse plasma", British Journal of Radiology, 2010, vol. 83, pp. 694-701.

Ziegler et al., "Circulating DNA: a new diagnostic gold mine?", Cancer Treatment Reviews, 2002, vol. 28, pp. 255-271.

Zilberstein et al., "Parallel isoelectric focusing chip", Proteomics, 2004, vol. 4(9), pp. 2533-2540.

Zilberstein et al., "Parallel isoelectric focusing II", Electrophoresis, 2004, vol. 25(21-22), pp. 3643-3651.

Zilberstein et al., "Parallel processing in the isoelectric focusing chip", Electrophoresis, 2003, vol. 24(21), pp. 3735-3744.

Zuo et al., "A method for global analysis of complex proteomes using sample prefractionation by solution isoelectrofocusing prior to two-dimensional electrophoresis", Analytical Biochemistry, 2000, vol. 284(2), pp. 266-278.

Phaneuf, C. R. et al., "Integrated LAMP and immunoassay platform for diarrheal disease detection," Biosensors and Bioelectronics (2018) 120:93-101.

* cited by examiner

US 10,981,174 B1

PROTEIN AND NUCLEIC ACID DETECTION FOR MICROFLUIDIC DEVICES

CROSS-REFERENCE TO RELATED APPLICATION

This application is a continuation-in-part of U.S. application Ser. No. 15/669,426, filed Aug. 4, 2017, which in turn claims the benefit of U.S. Provisional Application No. 62/370,843, filed Aug. 4, 2016. Each of these application is hereby incorporated by reference in its entirety.

STATEMENT OF GOVERNMENT INTEREST

This invention was made with Government support under Contract No. DE-NA0003525 awarded by the United States Department of Energy/National Nuclear Security Administration and under Grant No. R01AI098853 awarded by the National Institute of Allergy and Infectious Diseases of the National Institutes of Health. The Government has certain rights in the invention.

FIELD OF THE INVENTION

The present invention relates to methods for detecting targets by employing a temperature control system with a microfluidic device. The system allows for non-contact heating by employing an infrared emitter. In some instances, the system can be used in conjunction with a centrifugal microfluidic device. Optionally, a mask can be implemented to provide selective heating of desired assay areas of the device.

BACKGROUND OF THE INVENTION

For microfluidic systems, temperature control can provide enhanced modalities to control reaction rates, as well as to perform certain amplification reactions. Thus, there is a need for other heating systems capable of providing a simplified interface with a rotating device while efficiently controlling temperature.

For simultaneous detection of various targets, temperature can play a key role in assay design. For instance, nucleic acid tests can require an elevated temperature for the amplification process. However, protein tests tend to minimize elevated temperatures, which can denature and/or inactive protein targets or protein reagents. Accordingly, there is a need for selective control of heating to perform diverse assays.

SUMMARY OF THE INVENTION

The present invention relates to methods for detecting nucleic acid target and polypeptide targets by employing a non-contact temperature control system with a microfluidic device. In particular, the temperature control system allows for particular regions of the device to be selectively heated, while masking other regions to minimize heating. For instance, the system employs an infrared emitter to direct radiation to a surface of the device. A mask is employed to shield portions of the device from direct radiation.

Accordingly, in a first aspect, the invention features a method for detecting a nucleic acid target and a polypeptide target in a fluid sample, the method including: introducing the fluid sample to a detection system (e.g., any described herein, such as a detection system including a temperature control system, including any described herein); generating a plurality of first complexes on a plurality of first particles in the first assay area of a microfluidic device, where at least one first complex includes the nucleic acid target and a first label agent; generating a plurality of second complexes on a plurality of second particles in the second assay area of the microfluidic device, where at least one second complex includes the polypeptide target and a second label agent; transporting the plurality of first particles through a first density medium in the first assay area and the plurality of second particles through a second density medium in the second assay area; and detecting a signal from the first label agent of the first complex bound to the first particle and/or the second label agent of the second complex bound to the second particle.

In some embodiments, the plurality of first complexes and the plurality of second complexes can be generated sequentially in any order. In other embodiments, the plurality of first complexes and the plurality of second complexes can be simultaneously.

In some embodiments, generating the plurality of first complexes includes selectively heating the first assay area.

In some embodiments, the system (e.g., the detection system and/or the temperature control system) further includes a mask configured to be disposed between the emitter and the microfluidic device. In other embodiments, the mask includes an opening to provide selective heating of the first assay area of the microfluidic device and a shielded region to provide selective masking of the second assay area of the microfluidic device.

In some embodiments, the focal point is configured to be positioned on or within the first assay area containing a density medium. In other embodiments, the first assay area includes a narrowed region, and the focal point is configured to be positioned on or within the narrowed region.

In some embodiments, generating a plurality of first complexes step includes heating the first assay area with the emitter. In other embodiments, heating can include employing a mask to provide an opening in proximity to the first assay area and a shielded region in proximity to the second assay area.

In some embodiments, transporting includes spinning the microfluidic disc. In other embodiments, spinning can be in response to a motor control signal from a motor module configured to be coupled to the microfluidic disc.

In some embodiments, detecting includes detecting a signal from the first and/or second label agents present in the first and/or second assay area. In other embodiments, detecting can include employing a detection module, where the detection module is configured to generate an electronic detection signal based, at least in part, on the signal from the first and/or second label agents.

In some embodiments, the first density medium has a density lower than a density of the plurality of first particles and higher than a density of the fluid sample within the first assay area. In other embodiments, the first assay area further includes a further density medium, a plurality of cells, a plurality of sedimentation particles, and/or a separation layer fluid.

In some embodiments, the second density medium has a density lower than a density of the plurality of second particles and higher than a density of the fluid sample within the second assay area. In other embodiments, the second assay area further includes a further density medium, a plurality of cells, a plurality of sedimentation particles, and/or a separation layer fluid.

In some embodiments, at least one first complex includes the nucleic acid target hybridized to the first label agent, in which the first label agent is bound to at least one first particle. In some embodiments, the first label agent includes a nucleic acid portion configured to hybridize to a sequence of the nucleic acid agent and a detectable label. In other embodiments, the first label agent includes a first end, a second end, and a nucleic acid portion disposed between the first and second ends, in which the first end includes a detectable label (e.g., a fluorophore), the nucleic acid portion is configured to hybridize to a sequence of the nucleic acid agent, and the second end includes a functional group configured to bind to a surface of a particle. In other embodiments, the first label agent can be configured to be used in conjunction with a quencher agent configured to hybridize to the first label agent, to quench the detectable signal from the detectable and to be released in the presence of the nucleic acid target.

In some embodiments, at least one first complex includes the nucleic acid target bound to a cationic surface of at least one first particle, where the first label agent is bound to the nucleic acid target. Exemplary first label agents can include a nucleic acid probe (e.g., a nucleic acid portion attached to a detectable label by a linker, such as a covalent bond).

In other embodiments, at least one second complex includes the polypeptide target bound to a capture agent disposed on a surface of at least one second particle, where the second label agent is bound to the polypeptide target. Exemplary second label agents can include a detection antibody (e.g., an antibody portion attached to a detectable label by a linker, such as a covalent bond).

In a second aspect, the present invention features a method for detecting a nucleic acid target in a fluid sample, the method including introducing the fluid sample to a system (e.g., any described herein); generating a plurality of first complexes on a plurality of first particles in the first assay area, where at least one first complex includes the nucleic acid target and a first label agent; transporting the plurality of first particles through a first density medium in the first assay area; and detecting a signal from the first label agent of the first complex bound to the first particle.

In some embodiments, generating includes selectively heating the first assay area by employing the mask and the emitter.

In some embodiments, the system includes a microfluidic disc including a substrate and a first assay area, which is disposed, at least in part, within or on the substrate; and a non-contact temperature control system for the microfluidic device, where the temperature control system including an infrared emitter configured to emit at a wavelength of from about 1 µm to about 5 µm and positioned to direct radiation to a first surface of the microfluidic device, and where a focal point of the emitter configured to be positioned on or within the first assay area, or a portion thereof, of the microfluidic device.

In a third aspect, the present invention features a method for detecting a nucleic acid target and a polypeptide target in a fluid sample, the method including: introducing the fluid sample to a system; generating a plurality of first complexes on a plurality of first particles in the first assay area, where at least one first complex includes the nucleic acid target and a first label agent, where the generating includes selectively heating the first assay area by employing a mask and an emitter; generating a plurality of second complexes on a plurality of second particles in the second assay area, where at least one second complex includes the polypeptide target and a second label agent, in which the plurality of first complexes and the plurality of second complexes can be generated sequentially in any order or simultaneously; transporting the plurality of first particles through a first density medium in the first assay area and the plurality of second particles through a second density medium in the second assay area; and detecting a signal from the first label agent of the first complex bound to the first particle and/or the second label agent of the second complex bound to the second particle.

In some embodiments, the system includes a microfluidic disc including a substrate, a first assay area, and a second assay area, in which each of the first and second assay areas is disposed, at least in part, within or on the substrate; a non-contact temperature control system for the microfluidic device, where the temperature control system including an infrared emitter configured to emit at a wavelength of from about 1 µm to about 5 µm and positioned to direct radiation to a first surface of the microfluidic device, and where a focal point of the emitter configured to be positioned on or within the first assay area, or a portion thereof, of the microfluidic device; and a mask configured to be disposed between the emitter and the microfluidic device, where the mask includes an opening to provide selective heating of the first assay area of the microfluidic device and a shielded region to provide selective masking of the second assay area of the microfluidic device.

In any embodiment herein, the microfluidic disc includes a substrate, where the substrate at least in part defines a channel; a sample port in fluid communication with the channel and configured to receive a plurality of particles (e.g., first particles and/or second particles) in a fluid sample; and a detection region coupled to the channel and defined at least in part by the substrate and configured to contain a density medium, where the density medium has a density lower than the plurality of particles and higher than a density of the fluid sample. In some embodiments, the channel and detection region are configured to transport the plurality of particles in the fluid sample from the channel through the density medium responsive to a centrifugal force, where at least a portion of the fluid sample is restricted from transport through the density medium.

In any embodiment herein, the plurality of first and second complexes are generated simultaneously.

In any embodiment herein, the detection system includes: a microfluidic disc including a substrate, a first assay area, and a second assay area, in which each of the first and second assay areas is disposed, at least in part, within or on the substrate. In some embodiments, the detection system further includes a non-contact temperature control system (e.g., any described herein).

In any embodiment herein, the detection system can include a non-contact temperature control system for the microfluidic device, where the temperature control system includes an infrared emitter configured to emit at a wavelength of from about 1 µm to about 5 µm and positioned to direct radiation to a first surface of the microfluidic device. In some embodiments, a focal point of the emitter is configured to be positioned on or within the first assay area, or a portion thereof, of the microfluidic device.

In any embodiment herein, the temperature control system can include a reflector configured to reflect radiation that is collected from a second surface of the microfluidic device, where the second surface opposes the first surface. In some embodiments, the focal point of the emitter and a vertex of the reflector are aligned along a central axis. In other embodiments, the focal point is configured to be positioned on or within the assay area (e.g., the first and/or second assay area) containing a density medium. In some embodiments, the assay area includes a narrowed region, and the focal point is configured to be positioned on or within the narrowed region.

In any embodiment herein, the detection system and/or the temperature control system further includes a mask configured to be disposed between the emitter and the microfluidic device. In some embodiments, the mask includes an opening to provide selective heating of the first assay area of the microfluidic device and a shielded region to provide selective masking of the second assay area of the microfluidic device.

In any embodiment herein, the temperature control system further includes a cooling fan configured to be in proximity to the emitter. In some embodiments, the emitter and the cooling fan are configured to be positioned above the microfluidic device. In further embodiments, the reflector and the detection module are configured to be positioned below the microfluidic device.

In any embodiment herein, the detection system and/or the temperature control system further a detection module configured to detect a signal from the assay area.

In any embodiment herein, the emitter has a peak wavelength of from about 2 µm to about 3 µm.

In any embodiment herein, the system (e.g., the detection system or the temperature control system) includes a microfluidic disc (e.g., including a substrate; and an assay area disposed, at least in part, within or on the substrate); an infrared emitter (e.g., configured to emit at a wavelength of from about 1 µm to about 5 µm and positioned to direct radiation to a first surface of the microfluidic device, where a focal point of the emitter configured to be positioned on or within an assay area, or a portion thereof), of the microfluidic device; a motor module (e.g., configured to be coupled to the microfluidic disc and to spin the microfluidic disc in response to a motor control signal); and a detection module (e.g., configured to detect a signal from one or more label agents present in the assay area, where the detection module is configured to generate an electronic detection signal based, at least in part, on the signal from the one or more label agents). In some embodiments, the system further includes a reflector, e.g., configured to reflect radiation that is collected from a second surface of the microfluidic device, where the second surface opposes the first surface, where the focal point of the emitter and a vertex of the reflector are aligned along a central axis.

In any embodiment herein, the system (e.g., the detection system or the temperature control system) includes a processing device (e.g., coupled to the motor module and the detection module). In some embodiments, the processing device is configured to generate the motor control signal and provide the motor control signal to the motor module. In other embodiments, the processing device is further configured to receive the electronic detection signal from the detection module.

In any embodiment herein, the non-contact temperature control module includes an infrared emitter configured to emit at a wavelength of from about 1 µm to about 5 µm and positioned to direct radiation to a first surface of the microfluidic device; a reflector configured to reflect radiation that is collected from a second surface of the microfluidic device; and a focal point of the emitter configured to be positioned on or within the detection region, or a portion thereof, of the microfluidic device, where the second surface opposes the first surface, and where the focal point of the emitter and a vertex of the reflector are aligned along a central axis.

In any embodiment herein, the motor module is configured to be coupled to the microfluidic disc, to receive a motor control signal, and to spin the microfluidic disc responsive to the motor control signal.

In any embodiment herein, the detection module is positioned to detect a signal from one or more label agents affixed to the plurality of particles, where the detection module is configured to generate an electronic detection signal based, at least in part, on the signal from the one or more label agents.

In any embodiment herein, the processing device is coupled to the motor module and the detection module, where the processing device is configured to generate the motor control signal and provide the motor control signal to the motor module, and where the processing device is further configured to receive the electronic detection signal from the detection module.

In any embodiment herein, the system (e.g., the detection system or the temperature control system) includes an upper enclosure (e.g., configured to contain the emitter) and a lower enclosure (e.g., configured to contain the reflector, the motor module, and the detection module). In some embodiments, the upper enclosure is further configured to contain a cooling fan and maintain the cooling fan in proximity to the emitter. In other embodiments, the lower enclosure is further configured to contain the microfluidic disc.

Definitions

As used herein, the term "about" means +/−10% of any recited value. As used herein, this term modifies any recited value, range of values, or endpoints of one or more ranges.

By "fluidic communication," as used herein, refers to any duct, channel, tube, pipe, chamber, or pathway through which a substance, such as a liquid, gas, or solid may pass substantially unrestricted when the pathway is open. When the pathway is closed, the substance is substantially restricted from passing through. Typically, limited diffusion of a substance through the material of a plate, base, and/or a substrate, which may or may not occur depending on the compositions of the substance and materials, does not constitute fluidic communication.

By "microfluidic" or "micro" is meant having at least one dimension that is less than 1 mm. For instance, a microfluidic structure (e.g., any structure described herein) can have a length, width, height, cross-sectional dimension, circumference, radius (e.g., external or internal radius), or diameter that is less than 1 mm.

As used herein, the terms "top," "bottom," "upper," "lower," "above," and "below" are used to provide a relative relationship between structures. The use of these terms does not indicate or require that a particular structure must be located at a particular location in the apparatus.

The terms "polynucleotide" and "nucleic acid," used interchangeably herein, refer to a polymeric form of nucleotides of any length, either ribonucleotides or deoxyribonucleotides. Thus, this term includes, but is not limited to, single-stranded (e.g., sense or antisense), double-stranded, or multi-stranded ribonucleic acids (RNAs), deoxyribonucleic acids (DNAs), threose nucleic acids (TNAs), glycol nucleic acids (GNAs), peptide nucleic acids (PNAs), locked nucleic acids (LNAs), or hybrids thereof, genomic DNA, cDNA, DNA-RNA hybrids, or a polymer comprising purine and pyrimidine bases or other natural, chemically or biochemically modified, non-natural, or derivatized nucleotide bases. Polynucleotides can have any useful two-dimensional or three-dimensional structure or motif, such as regions including one or more duplex, triplex, quadruplex, hairpin, and/or pseudoknot structures or motifs. For any nucleic acid sequence described herein, uracil (U) may be thymine (T), and T may be U.

"Complementarity" or "complementary" refers to the ability of a nucleic acid to form hydrogen bond(s) with another nucleic acid sequence by either traditional Watson-Crick or other non-traditional types, e.g., form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. As is known in the art, standard Watson-Crick base-pairing includes: adenine (A) pairing with thymine (T), adenine (A) pairing with uracil (U), and guanine (G) pairing with cytosine (C). In addition, it is also known in the art that for hybridization between two RNA molecules (e.g., dsRNA), guanine (G) base pairs with uracil (U). A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" or "sufficient complementarity" as used herein refers to a degree of complementarity that is at least 60%, 65%, 70%, 75%, 80%, 85%, 90%, 95%. 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part 1, Second Chapter, "Overview of principles of hybridization and the strategy of nucleic acid probe assay," Elsevier, N.Y.

"Hybridization" or "hybridize" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence. A "complement" can include a "reverse complement," in which a given sequence is reversed to provide a reverse sequence and then a complement, as defined herein, of that reverse sequence provides a reverse complement. Hybridization and washing conditions are well known and exemplified in Sambrook J, Fritsch E F, and Maniatis T, "Molecular Cloning: A Laboratory Manual," Second Edition, Cold Spring Harbor Laboratory Press, Cold Spring Harbor (1989), particularly Chapter 11 and Table 11.1 therein; and Sambrook J and Russell W, "Molecular Cloning: A Laboratory Manual," Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementation, variables well known in the art. The greater the degree of complementation between two nucleotide sequences, the greater the value of the melting temperature (Tm) for hybrids of nucleic acids having those sequences. For hybridizations between nucleic acids with short stretches of complementarity (e.g., complementarity over 35 or less, 30 or less, 25 or less, 22 or less, 20 or less, or 18 or less nucleotides) the position of mismatches becomes important (see Sambrook et al., supra, 11.7-11.8). Typically, the length for a hybridizable nucleic acid is at least about 10 nucleotides. Illustrative minimum lengths for a hybridizable nucleic acid are: at least about 15 nucleotides; at least about 20 nucleotides; at least about 22 nucleotides; at least about 25 nucleotides; and at least about 30 nucleotides). Furthermore, the skilled artisan will recognize that the temperature and wash solution salt concentration may be adjusted as necessary, according to factors such as length of the region of complementation and the degree of complementation.

It is understood in the art that the sequence of polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a loop structure or hairpin structure). A polynucleotide can comprise at least 70%, at least 80%, at least 90%, at least 95%, at least 99%, or 100% sequence complementarity to a target region within the target nucleic acid sequence to which they are targeted. For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. Percent complementarity between particular stretches of nucleic acid sequences within nucleic acids can be determined routinely using BLAST programs (basic local alignment search tools) and PowerBLAST programs known in the art (Altschul S F et al., *J. Mol. Biol.* 1990; 215:403-10; Zhang J et al., *Genome Res.* 1997; 7:649-56) or by using the Gap program (Wisconsin Sequence Analysis Package, Version 8 for Unix, Genetics Computer Group, University Research Park, Madison Wis.), using default settings, which uses the algorithm of Smith T F et al., *Adv. Appl. Math.* 1981; 2(4):482-9).

By "protein," "peptide," or "polypeptide," as used interchangeably, is meant any chain of more than two amino acids, regardless of post-translational modification (e.g., glycosylation or phosphorylation), constituting all or part of a naturally occurring polypeptide or peptide, or constituting a non-naturally occurring polypeptide or peptide, which can include coded amino acids, non-coded amino acids, modified amino acids (e.g., chemically and/or biologically modified amino acids), and/or modified backbones.

By "attaching," "attachment," or related word forms is meant any covalent or non-covalent bonding interaction between two components. Non-covalent bonding interactions include, without limitation, hydrogen bonding, ionic interactions, halogen bonding, electrostatic interactions, π bond interactions, hydrophobic interactions, inclusion complexes, clathration, van der Waals interactions, and combinations thereof. Two components can be attached by any useful linker described herein.

By "linker" is meant any useful multivalent (e.g., bivalent) component useful for joining to different portions or segments. Exemplary linkers include a nucleic acid sequence, a chemical linker, etc. The linker may include a covalent linker or a non-covalent linker. In some embodiments: the linker may comprise a flexible arm, e.g., 2, 3, 4, 5, 6, 7, 8, 9, 10, 11, 12, 13, 14, or 15 carbon atoms. Exemplary linkers include BS3 ([bis(sulfosuccinimidyl)suberate]; BS3 is a homobifunctional N-hydroxysuccinimide ester that targets accessible primary amines), NHS/EDC (N-hydroxysuccinimide and N-ethyl-'(dimethylaminopropyl)carbodimide; NHS/EDC allows for the conjugation of primary amine groups with carboxyl groups), sulfo-EMCS ([N-e-Maleimidocaproic acid]hydrazide; sulfo-EMCS are heterobifunctional reactive groups (maleimide and NETS-ester) that are reactive toward sulfhydryl and amino groups), hydrazide (most proteins contain exposed carbohydrates and hydrazide is a useful reagent for linking carboxyl groups to primary amines), and SATA (N-succinimidyl-S-acetylthioacetate; SATA is reactive towards amines and adds protected sulfhydryls groups). Examples of other suitable linkers are succinic acid, Lys, Glu, Asp, a dipeptide such as Gly-Lys, an α-helical linker (e.g., A(EAAAK)$_n$A, where n is 1, 2, 3, 4, or 5), an alkyl chain (e.g., an optionally substituted $C_{1-12}$ alkylene or alkynyl chain), or a polyethylene glycol (e.g., $(CH_2CH_2O)_m$, where m is from 1 to 50).

Other features and advantages of the invention will be apparent from the following description and the claims.

DETAILED DESCRIPTION OF THE INVENTION

The present invention relates to methods of employing a non-contact temperature control system for a microfluidic device (e.g., a microfluidic disc). The system can allow for detecting various targets (e.g., simultaneous detection of a nucleic acid target and a polypeptide target) on a single device (e.g., a centrifugal microfluidic disc).

In particular, the system employs an infrared emitter to provide non-contact heating, which can be especially useful when employed with a device configured to be rotated (e.g., as in a centrifugal device) and/or configured to perform centrifugal sedimentation-based assays. Optionally, the system can include other modules (e.g., a motor module, a detection module, and/or a processing device) to facilitate use of the microfluidic device to perform any useful analysis or assay (e.g., any described herein).

Various other components can be employed to increase heating efficiency (e.g., by employing a reflector to reflect radiation back to the heated surface), to provide selective heating of a particular portion of the device (e.g., by employing a mask, as described herein), and/or to cool the heating element (e.g., by employing a cooling fan). The system can include other modules to rotate the device and/or to detect one or more targets within an assay area of the idea. The present invention also encompasses an integrated system, in which various enclosures can be configured to house the components and the enclosures themselves are configured to provide a contained system.

Figure 1A:
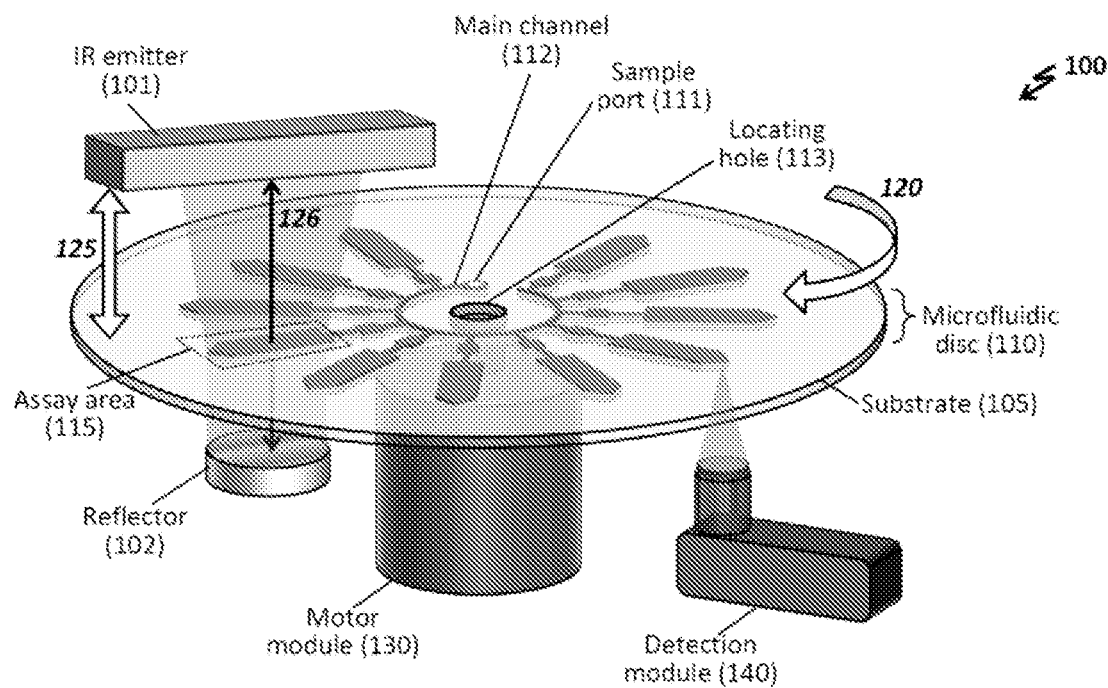
FIG. 1A-1B shows an exemplary non-contact temperature control system for a microfluidic device. Provided is a schematic of an exemplary system 100 including an infrared emitter 101 (FIG. 1A). Also provided is a thermal image of the top surface of the heated disc provided a reference point for temperature monitoring (FIG. 1B), in which region 1 overlies the assay areas of the disc.

FIG. 1A provides an exemplary non-contact temperature control system 100 for a microfluidic device. As can be seen, the system includes an infrared emitter 101 and a reflector 102 configured to reflect radiation. The emitter and reflector can be positioned, relative to the microfluidic device (e.g., a microfluidic disc 110), in any useful manner. In one instance, the emitter 101 is positioned to direct radiation to a first surface (e.g., a top surface) of the microfluidic disc 110, and the reflector 102 is positioned to collect radiation from a second surface (e.g., a bottom surface) of the microfluidic disc 110, where the second surface opposes the first surface. In addition, the focal point of the emitter can configured to be positioned on or within an assay area 115, or a portion thereof. The emitter can be configured to emit any useful wavelength, e.g., such as a wavelength of from about 1 µm to about 5 µm (e.g., from 1 µm to 4 µm, 1 µm to 3 µm, 2 µm to 5 µm, 2 µm to 4 µm, or 2 µm to 3 µm).

Figure 1B:
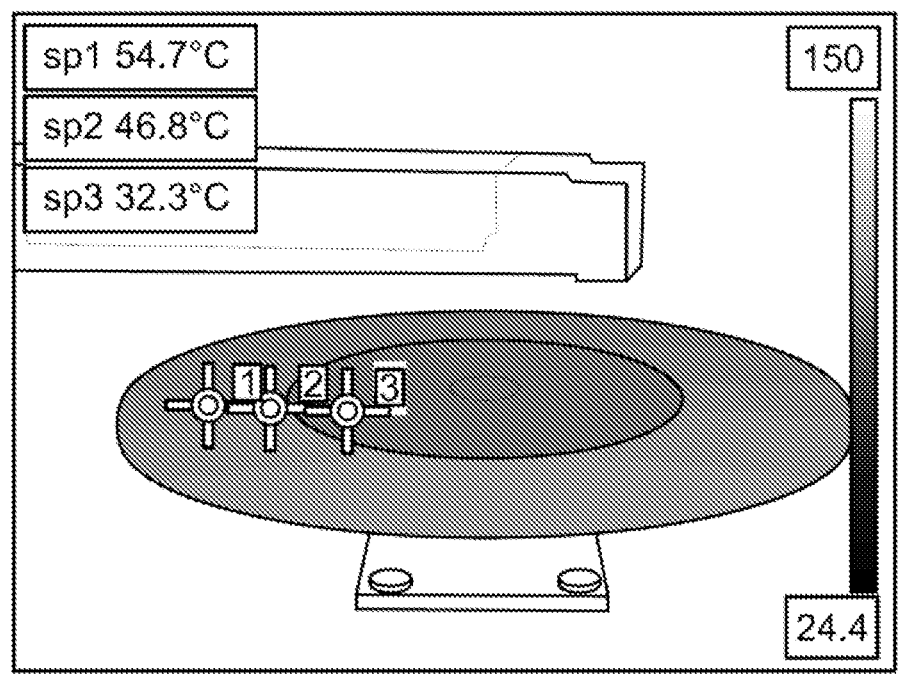

The positions of the emitter and reflector can be aligned along any useful axis. In one instance, the focal point of the emitter 101 and a vertex of the reflector 102 are aligned along a central axis 126. In another instance, the distance 125 between the emitter and the focal point of the emitter can be optimized to provide uniform heating and/or the desired heating temperature. In yet another instance, the emitter is positioned above the assay area of the microfluidic device. As seen in FIG. 1B, position 1 corresponds to a position above the assay area of the device, positions 2 and 3 correspond to positions located towards the center of the device.

The microfluidic device can have any useful structural features. In one instance, the device is a microfluidic disc 110 having a plurality of assay areas 115 disposed within or upon the substrate 105. Each assay area 115 can be in fluidic communication with a sample port 111 configured to provide a sample (e.g., a fluid sample) or a portion thereof (e.g., a fraction or a particular volume of the sample) to the assay area. Fluidic communication can include the use of a main channel 112 connecting the sample port 111 directly or indirectly to an assay area 115. Indirect fluidic communication can include the use of intervening chamber(s) or valve(s) of any useful geometry or fluidic connection (e.g., any chamber described herein, such as reservoirs, channels, etc.). The disc 110 can further include any useful structure, such as a locating hole 113 or a tooth element, to interact with the motor module 130 configured to rotate 120 the disc 110.

Modules can be positioned to ensure efficient and/or effective heating of the disc. In one embodiment, the emitter is positioned opposite of the reflector. In another embodiment, as seen in FIG. 1A, the motor module 130 and the detection module 140 are positioned opposite of the emitter 101 (e.g., on opposing sides of the disc 110) to reduce thermal damage to the motor and/or detection components. In addition, the emitter and the detection module can be positioned on opposing lateral sides. As seen in FIG. 1A, the emitter 101 is positioned on one lateral side of the disc 110, and the detection module 140 is positioned on the opposing lateral side of the emitter 101.

Figure 2A:
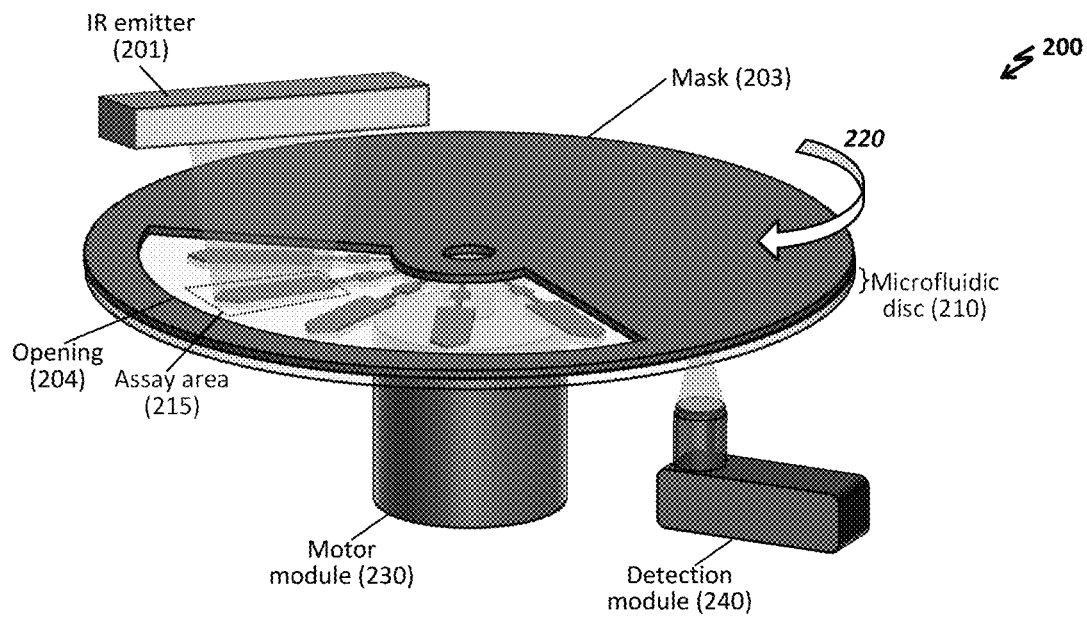
FIG. 2A-2B shows another exemplary non-contact temperature control system. Provided are schematics of an exemplary system 200 including a mask 203 (FIG. 2A) and a disc 210 having a plurality of assay areas 215 labeled A1 to A11 (FIG. 2B).

The system can include one or more additional structural features to selectively heat portions of the device. As seen in FIG. 2A, the system 200 can include an infrared emitter 201 and a mask 203 (e.g., an optically opaque mask) configured to include an opening 204. By positioning the opening 204 above a particular assay area 215, that area is selectively heated by the emitter 201. The remaining shielded portions of the disc 210 will not be heated. If the mask 203 is configured to rotate with the disc 210, then selective heating can be maintained during rotation 220 by the motor module 230. The mask 203 can be provided to be in proximity to a first surface (e.g., the top surface) of the disc 210, and the detection module 240 can be provided to be in proximity to a second surface (e.g., the bottom surface) of the disc 210, in which the second surface opposes the first surface. In this way, the mask will not interfere with the detection signal to be detected by the detection module.

Figure 2B:
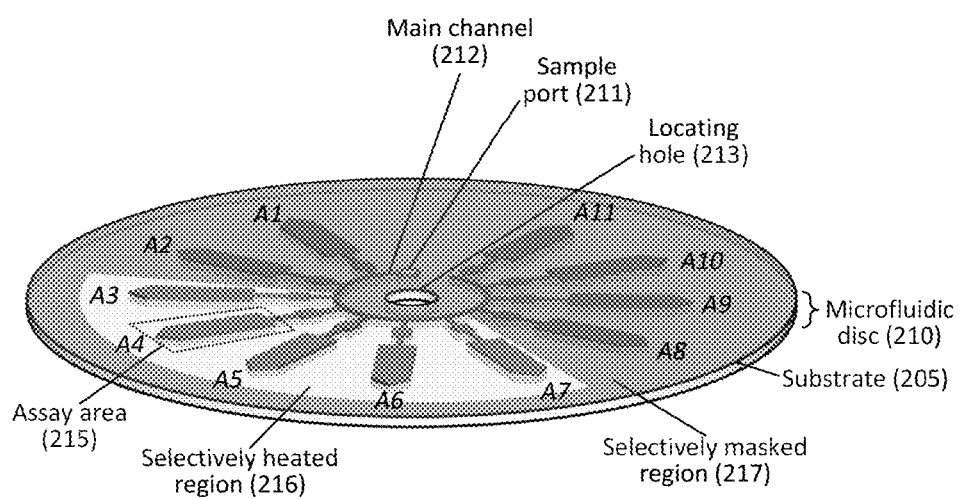

The mask can be further configured to provide selective heating of any portion of the disc. As seen in FIG. 2B, the mask can be configured to provide an opening that defines the selectively heated region 216 of the substrate 205 and to provide a shielded portion that defines the selectively masked region 217 of the substrate 205. Any useful number of assay areas 215 can be exposed within the opening. As seen in FIG. 2B, assay areas A3-A7 are exposed within the opening, thus these areas constitute the selectively heated region 216. Other assay areas A1, A2, A8-A11 are shielded and will not be heated by the focal point of the emitter.

The mask can include one or more openings, which can be provided in any useful spatial pattern to provide selective heating of any useful portion of the microfluidic disc. In addition, the mask can include any useful shielded portion to protect any portion of the disc from extensive heating. In one embodiment, the mask can include shielded regions over the main channel 212 and/or the sample port 211 to reduce excessive heating of the sample, which can result in fluid leakage, pressure build-up, and/or sample deactivation. The mask can also include an alignment hole that aligns with the locating hole 213 of the disc 210, so that the mask and the disc can be aligned together and rotated along a central rotational axis of the motor module.

Figure 3A:
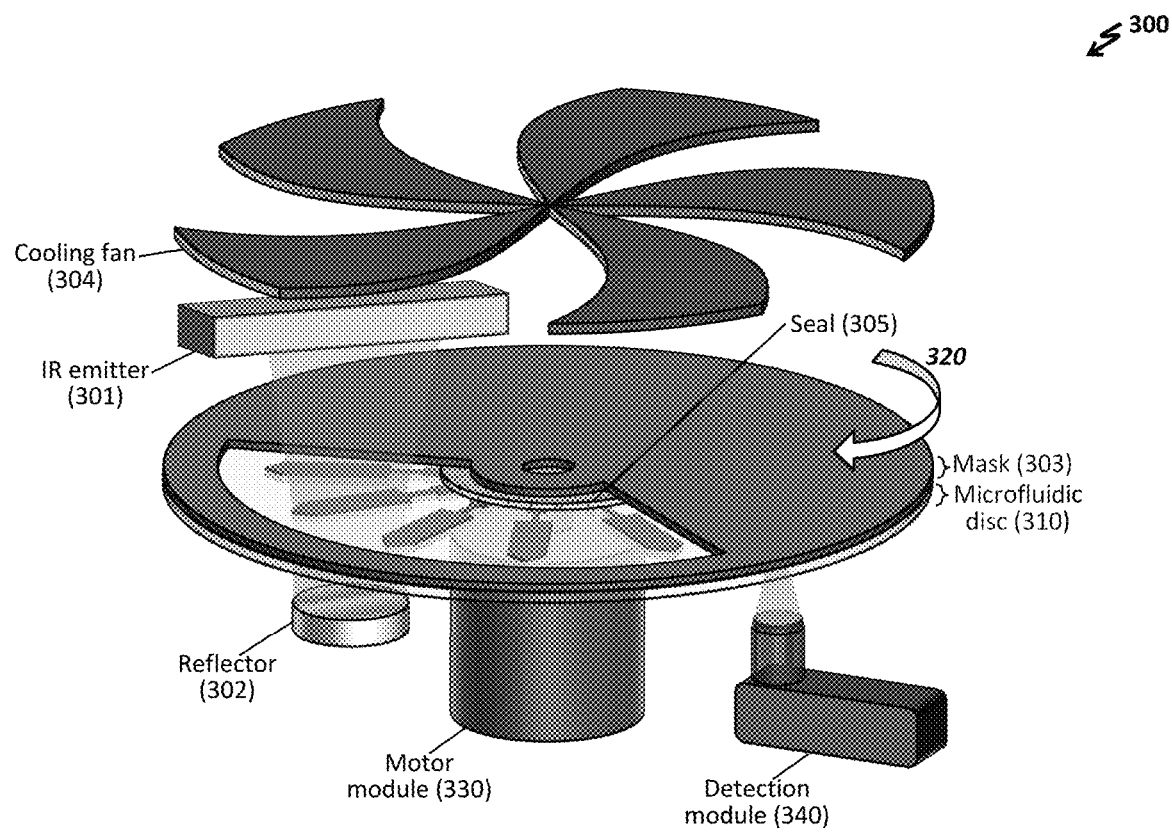
FIG. 3A-3C shows yet another exemplary non-contact temperature control system. Provided are schematics of an exemplary system 300 including a cooling fan 304 (FIG. 3A), another exemplary system 3000 provided within an upper enclosure 3010 and a lower enclosure 3015 (FIG. 3B), and yet another exemplary system 3100 provided within a hinged system having an upper enclosure 3110 and a lower enclosure 3115 (FIG. 3C).

The system may include other structural elements for use with the emitter. As seen in FIG. 3A, the system 300 can include a cooling fan 304 configured to be in proximity to the emitter 301. The system can also include a mask 303 to provide selective heating of assay areas, as well as a seal 305 disposed upon the microfluidic disc to minimize heating of portions of the microfluidic disc 310 that is not an assay area (e.g., minimize heating in proximity to the sample port and/or main channel). Further, the system can include a reflector 302 (e.g., as described herein). A motor module 330 can be configured to be coupled to the microfluidic disc 310 and to spin 320 the microfluidic disc in response to a motor control signal; and a detection module 340 can be configured to detect a signal from one or more label agents present in the assay area.

Figure 3B:
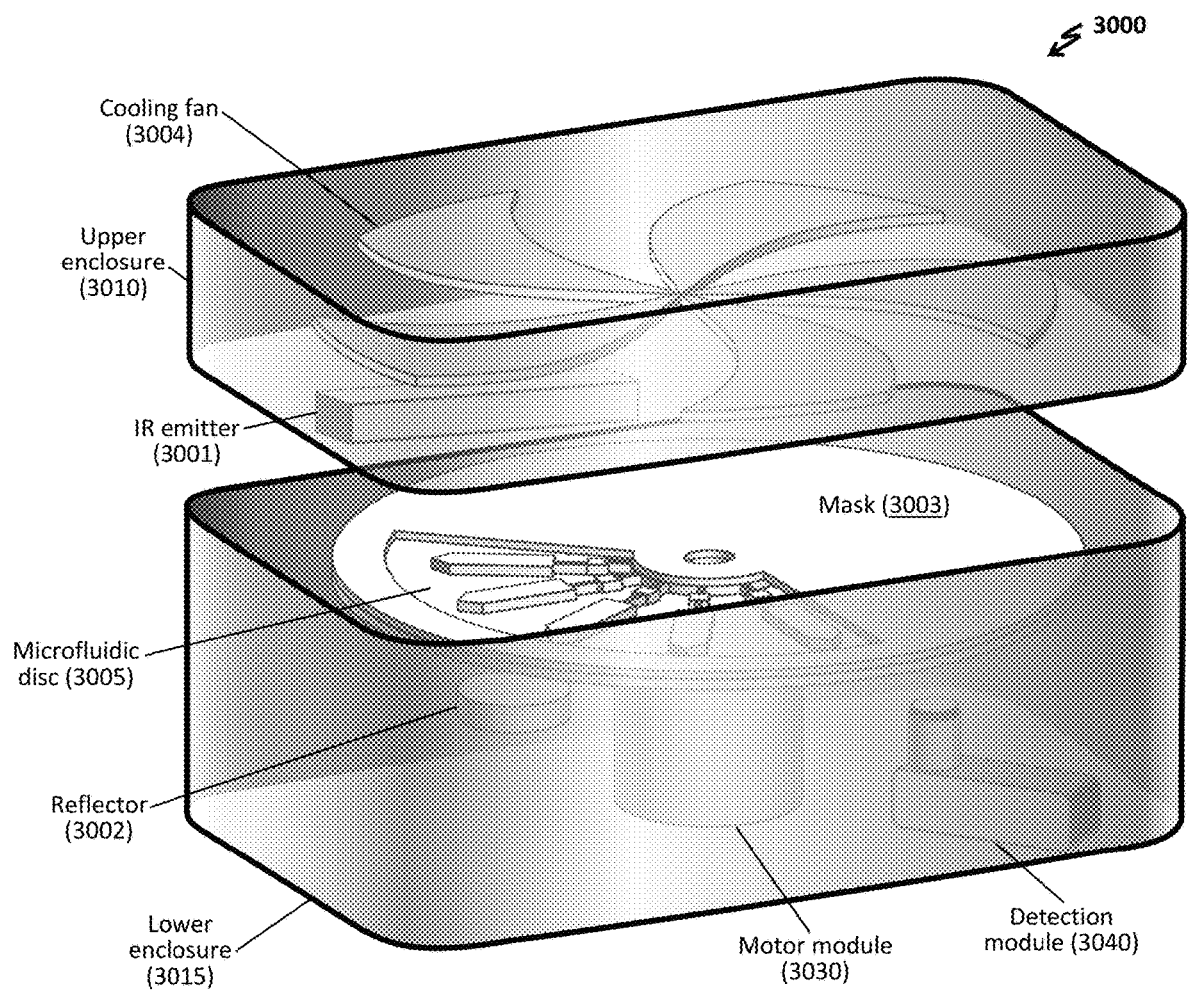

The system can be provided in any useful enclosure. As seen in FIG. 3B, the system 3000 can include an emitter 3001 and a cooling fan 3004 disposed in an upper enclosure 3010, which in turn is configured to close over a lower enclosure 3015. The lower enclosure 3015 can include the remaining components and modules, which are configured to be aligned with the emitter when the upper and lower enclosures are mated. The lower enclosure 3015 can include a motor module 3030 configured to provide an aligned microfluidic disc 3005 (e.g., as determined by the position of the focal point of the emitter, which can be configured to be positioned on or within an assay area, or a portion thereof, of the microfluidic disc 3005); a detection module 3040; and an aligned reflector 3002 (e.g., configured to reflect radiation that is collected from a second surface of the microfluidic disc 3005, where the second surface opposes the first surface at which the emitter is positioned to direct radiation, and/or where the focal point of the emitter and a vertex of the reflector are aligned along a central axis). An optional mask 3003 can be housed in the lower enclosure 3015.

Figure 3C:
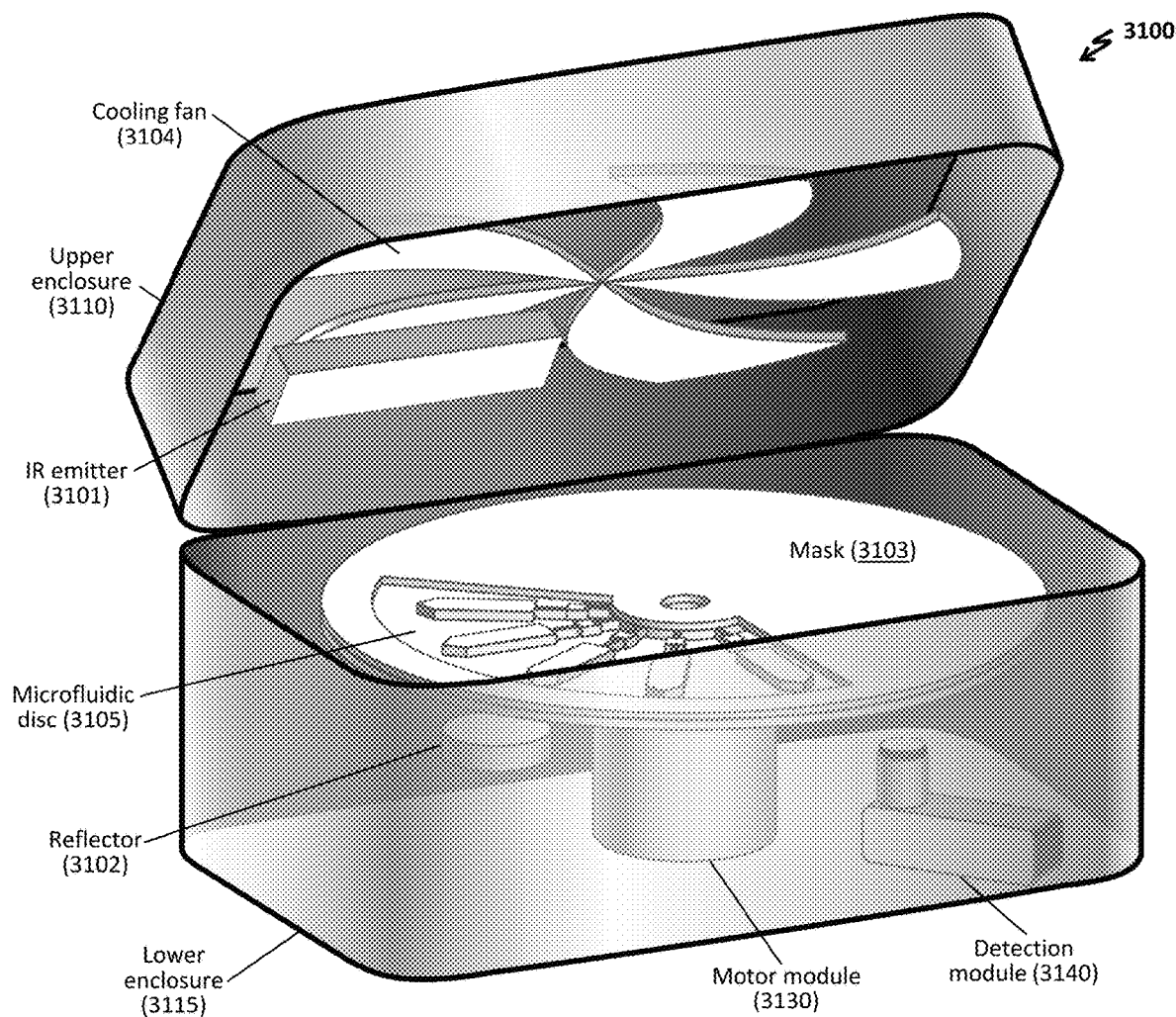

The upper and lower enclosures can interact in any useful manner. In one instance, the upper enclosure has an edge that mates with the edge of the lower enclosure (e.g., as in FIG. 3B). In another instance, the upper enclosure and lower enclosure are connected by way of a hinge (e.g., as in FIG. 3C). FIG. 3C provides a system 3100 including an emitter 3101 and a cooling fan 3104 disposed in an upper enclosure 3110, which in turn is configured to close over a lower enclosure 3015; a hinge disposed between the upper enclosure 3110 and the lower enclosure 3115; and a microfluidic disc 3105, an optional mask 3103, an aligned reflector 3102, a motor module 3130, and a detection module 3140 disposed in the lower enclosure 3115. Additional exemplary systems are provided in FIG. 4A-4D and FIG. 5A-5B.

Centrifugal Devices

A microfluidic disc can be operated as a centrifugal device. In some instances, the device includes a substrate that may at least partially define an assay region, as well as a port (e.g., a sample port or inlet port) configured to receive a sample. The port can be in fluidic communication with any useful chamber (e.g., within an assay area) or any useful region of the device (e.g., an assay area). During operation, a sample (e.g., a fluid sample including a plurality of particles, such as beads or cells) may be transported by applying a centrifugal force that is directed from an interior of the microfluidic disc toward a periphery of the microfluidic disc. The centrifugal force may be generated by rotating the microfluidic disc in any useful direction.

The device can be designed to facilitate multiplexed detection, in which multiple samples can be processed at the same time and/or each particular sample can be divided to be tested for multiple different targets. For instance, the device can include a plurality of assay areas configured for multiplexed and/or parallel detection.

Assay Areas, Including Detection Regions

An assay area includes any portion defined in part by a substrate, in which the assay area facilitates one or more reaction(s), separation(s), and/or detection of a desired target. The assay area can be defined by one or more chambers (e.g., a reagent chamber, an assay chamber, an incubation chamber, as well as channels connecting any useful chamber) in fluidic communication with a sample port configured to receive a test sample. The assay area can include a detection region, which can be a chamber (e.g., a channel) configured to allow for detection of a signal emitted by a label agent that can optionally be affixed directly or indirectly to the target and/or a particle (e.g., a bead or a cell).

During operation, a centrifugal force may generally be used to transport a fluid sample (optionally including particles) from an inlet port (e.g., a sample port) toward an assay area (e.g., a detection region of the assay region). Additionally, centrifugal forces may be used to transport density medium and/or particles from one or more reservoir(s) to the assay area.

The density medium can have a density greater than that of the fluid sample but lower than that of the particles to be detected. These differences in density can be employed to separate the particles from the fluid sample. By applying centrifugal force, flows are induced. Denser particles from the fluid sample are transported through the density medium, but the less dense components of the fluid sample are not transported through the density medium. In this manner, the particles (e.g., bound to one or more targets) are selectively separated from the remaining portions of the test sample, and detection limits can display improved sensitivity and/or selectivity.

The assay area can include a narrowed or tapered region, which can facilitate detection within the assay area. For instance, upon providing a centrifugal force, a sedimentation-based assay can be conducted within the assay area, such that a pellet is formed in a portion of the assay area closest to the edge of the microfluidic device. If this portion terminates in a narrowed or tapered region, then the pellet is distributed across a larger surface area, which may be more effective at transmitting a detection signal. In one instance, a fluorescence signal can be more easily detected across this narrowed region due to reduced scattering, thereby increasing the sensitivity of the assay. Accordingly, the assay area can have any useful dimension (e.g., width, height, radius, depth, etc.) and/or cross-section (e.g., rectangular, triangular, semi-circular, rounded, trapezoidal, etc.) that can be uniform or non-uniform along any axis or dimension. Further details on narrowed or tapered regions are described in U.S. Pat. No. 8,962,346, which is incorporated herein by reference in its entirety.

Chambers

The present apparatus (e.g., device, such as a microfluidic disc) can include one or more chambers, which can be configured to substantially enclose a fluid or a substance in the fluidic device (e.g., a microfluidic disc). Such chambers can include one or more ports (e.g., inlets or outlets), fluidic opening (e.g., vias), fluidic barriers, channels, or any other structure to allow for fluidic communication between one or more chambers, vents, etc. Exemplary chambers include a channel, a reservoir, etc., having any useful geometry or dimension.

The chambers can be designated for a particular use. Particular uses for such chambers include a sample chamber for receiving and/or storing a test sample, an incubation chamber for incubating a test sample, a reaction chamber for reacting a test sample or a processed sample with another reagent, a reagent chamber containing one or more reagents for detecting one or more targets (e.g., containing one or more label agents), a sterilization chamber containing one or more reagents to sterilize or disinfect the test sample (e.g., containing one or more sterilization agents, as described herein), an assay chamber for conducting one or more assays to detect one or more targets, a post-processing chamber to perform one or more procedures (e.g., lysis, polymerase chain reaction (PCR), amplification assay, immunoassay, analytic test, and/or biochemical analysis), and/or a waste chamber for storing one or more by-products of the assay. Each of these chambers can be interconnected by a valve (e.g., a passive valve, an active valve, an NC valve, and/or NO valve) and/or a channel that can optionally include such a valve in its fluidic path.

Substances and materials within a chamber can be transported to any other chamber in any useful manner. In one instance, rotation over a certain threshold results in transporting a reagent from a first chamber to another chamber (e.g., from a reservoir to a chamber in the assay area; or from a sample port to a reservoir; or from a sample port to a chamber in the assay area). In other instances, a channel can have a dimension that requires a certain rotation rate to overcome capillary pressure, such that the channel functions as a valve. In other instances, the channel includes a wax-based valve that requires melting for actuation. Other methods of controlling flow in microfluidic devices (e.g., pressure-induced flow, centrifugal force-driven flow, pumping, etc.) are known and can be implemented with the devices and systems herein.

Microfluidic Devices and Systems

An exemplary system can include one or more modules or components to facilitate performing assays with the microfluidic disc. In one non-limiting instance, the system includes a microfluidic disc, a motor module coupled to the disc and configured to spin the disc in order to generate centrifugal forces, a detection module positioned to detect a signal from one or more label agents in the assay area (e.g., within a detection region), and an optional processing device. An optional actuator may be coupled to the detection module and configured to move the detection module along the detection region in some examples.

In one instance, the motor module may be implemented using a centrifugation and/or stepper motor. The motor module may be positioned relative to the detection module, such that placing the disc on the motor ensures that an assay area, or a portion thereof, is exposed to the detection module. The motor module can include any useful motor, e.g., a brushed DC motor, a solenoid, a servo motor, a linear actuator, as well as combinations thereof, and a controller (e.g., a motor controller).

The detection module may include a detector (e.g., an electronic detector, an optical detector, a cell phone camera, a photodiode, a photomultiplier tube, and/or a CCD camera) suitable for detecting a signal from one or more label agents (e.g., affixed to particles to be detected and/or quantified). The detector module may include, for example, a laser and optics suitable for optical detection of fluorescence from fluorescent labels. In other examples, other detectors, such as electronic detectors, may be used. An optional actuator may move the detector to a variety of locations of the microfluidic disc (e.g., along the assay area) to detect a measurable signal. The one or more actuators may be coupled to the motor module and/or disc, such that the disc is moved relative to the detection module in response to signals from the processing device.

A processing device may be coupled to the motor module, the detection module, and/or the actuator. Furthermore, the processing device can be configured to provide one or more signals (e.g., one or more control signals to those modules and/or components), as well as to receive one or more signals (e.g., one or more electronic signals from the detection module corresponding to the presence or absence of label agent). All or selected components or modules may be housed in a common housing or in separate enclosures (e.g., optionally configured to operate together, such as by providing a hinged housing formed by connecting an upper enclosure to a lower enclosure by use of a hinge). The processing device can include any useful circuitry, control boards, switches (e.g., optical switches), power supply, input hubs, output hubs, etc. Microfluidic discs may be placed on the motor module and removed, such that multiple discs may be analyzed by the system.

The processing device may include one or more processing units, such as one or more processors. In some examples, the processing device may include a controller, logic circuitry, and/or software for performing functionalities described herein. The processing device may be coupled to one or more memories, input devices, and/or output devices including, but not limited to, disc drives, keyboards, mice, and displays. The processing device may provide control signals to the motor module to rotate the microfluidic disc at selected speeds for selected times. The processing device may provide control signals to the detection module (e.g., including one or more detectors and/or actuators), detect signals from the label agent(s), and/or move the detector to particular locations. The processing device may develop these control signals in accordance with input from an operator and/or in accordance with software. The software may include one or more executable instructions (e.g., stored on one or more memories) configured to cause the processing device to output a predetermined sequence of control signals, to perform one or more calculations (e.g., determine the presence or absence of a target based on electronic signals from the detection module), to communicate any useful output (e.g., a result, a setpoint, a level, etc.) over a network, to store any useful output in memory, and/or display any useful output on a display module. It is to be understood that the configuration of the processing device and related components is quite flexible, and any of a variety of computing systems may be used including server systems, desktops, laptops, controllers, and the like.

The system can include any other modifications to facilitate rotation of the device and/or detection within the device. In one instance, the device includes a structure configured to align an assay area with a detection module. In one non-limiting embodiment, an assay area can include a corresponding tooth element. In another non-limiting embodiment, each assay area includes a corresponding tooth element. In yet another non-limiting embodiment, one tooth element can be an extended tooth element having a different dimension than another tooth element. In use, the system can include a device including a plurality of assay regions and corresponding tooth elements; a motor module configured to move the device such that the assay areas move along a first path (e.g., a circular path disposed on a surface of the device)

and the tooth elements move along a second path (e.g., a circular path disposed on an edge or along a periphery of the device); an impinging element configured for placement in a first position that allows for movement of device and a second position, wherein the impinging element engages at least one tooth element when in the second position; a detection module configured to detect a signal (e.g., arising the detection region or the assay area; arising from one or more label agents or one or more targets); and processing device (e.g., a controller) communicatively coupled to the impinging element and the motor module, where the processing device is configured to provide a control signal to the impinging element to place the impinging element in the first position or the second position. In some embodiments, the detection module is positioned such that when the impinging element is in the second position, the detection module is aligned with at least one of the plurality of assay regions.

Exemplary devices (e.g., apparatuses) and systems, as well as methods employing such devices and systems, are described in U.S. Pat. Nos. 8,945,914, 8,962,346, 9,186,668, 9,244,065, 9,304,128, 9,304,129, 9,500,579, 9,702,871, 9,766,230, 9,795,961, 9,803,238, 9,903,001, 10,024,849, and 10,254,298, as well as U.S. Pat. Appl. Pub. Nos. 2015/0360225, 2018/0037960, and 2018/0065118, each of which is incorporated herein by reference in its entirety.

Density Medium and Particles

The present invention can be employed with any useful agents, including a density medium, a particle, as well as combinations thereof. The density medium may have a density lower than a density of a plurality of particles (e.g., beads or cells) and higher than a density of the fluid sample. The density medium may generally be implemented using a fluid having a density selected to be in the appropriate range, e.g., lower than a density of the particles to be detected or quantified and higher than a density of the fluid sample. In some examples, a fluid sample may be diluted for use with a particular density medium. The density medium may include, for example, a salt solution containing a suspension of silica particles, which may be coated with a biocompatible coating (e.g., a polyvinylpyrrolidone (PVP) coating or a silane coating). Examples of suitable density media are Percoll™ (colloidal silica coated with PVP), Percoll™ PLUS (colloidal silica coated with silane), Ficoll™ PM70 (high molecular weight sucrose-polymers with an average molecular weight of 70,000), Ficoll™ PM400 (a synthetic neutral, highly-branched hydrophilic polymer of sucrose with an average molecular weight of 400,000), Ficoll-Paque™ PLUS (a combination of Ficoll™ PM400, sodium diatrizoate, and disodium calcium EDTA), and Ficoll-Paque™ Premium (a combination of Ficoll™ PM400, sodium diatrizoate, and disodium calcium EDTA in water for injection), each of which is available from GE Healthcare Life Sciences, Little Chalfont, Buckinghamshire, United Kingdom. Particular densities may be achieved by adjusting a percentage of the density medium in a salt solution. Generally, viscosity and density of the density medium may be adjusted by selecting a composition of the medium. Varying the concentration of solutes such as sucrose or dextran in the medium may adjust the density and/or viscosity.

In some instances, sedimentation assays can be conducted, in which the settling velocity of a particle is described by known Stoke's flow equations. Sedimentation rates typically scale with a square of a particle's radius and can be linearly dependent with the difference in density between a particle and a surrounding fluid (e.g., as provided by a sample or by a density medium). Thus, under certain conditions, a population of particles can be separated according to its density and/or radius.

Particles of different sizes can be employed, in which the different sedimentation rates can be used to allow size-based separation and/or detection. The sedimentation rate of a particle is dependent on various characteristics of the particle, including particle size, particle surface charge, and/or particle density. Sedimentation can occur under any force, such as gravitational force or centrifugal force (e.g., by rotating or spinning a microfluidic device). In one non-limiting example, a first population of particles (e.g., having a first particle size and/or first particle density) can include a first type of capture agent, and a second population of particles (e.g., having a second particle size and/or second particle density) can include a second type of capture agent, thereby allowing for different sedimentation rates and/or separation zones for each population. For instance, smaller and/or less dense particles can be localized in a first separation zone, and larger and/or more dense particles can be localized in a second separation zone, thereby allowing for separation of different populations of particles by employing centrifugal force. Further details on sedimentation assays are provided in U.S. Pat. No. 8,945,914, which is incorporated herein by reference in its entirety.

Particles can be composed of any useful material and have any useful chemical properties (e.g., surface charge, including a positively charged surface or a negatively charged surface). Exemplary materials include polystyrene, polymethylmethacrylate, silica, metal (e.g., gold, iron, or iron oxide), as well as combinations thereof and coated versions thereof (e.g., including a polymer coating, a charged coating, or a coating including binding groups, such reactive linkers, antibodies, integrins, and/or selectins). Particles can have any useful dimension (e.g., as in microparticles, nanoparticles, etc.) depending on their use. For example, particle dimensions may be useful for use as sedimentation particles, whereas other dimensions or characteristics for use as labeling particles. In one non-limiting instance, a sedimentation particle can be modified to bind to certain cells, thereby increasing the sedimentation rate of certain cells upon binding and allowing these certain cell types to be selectively removed from the sample during centrifugation.

Other substances or reagents can be employed in conjunction with the density medium and/or a population of particles. In one instance, a separation layer fluid is employed, which forms an interface between a density medium and a sample, between a sample and a particle, and/or between the density medium and the particle. This separation layer fluid can have nay useful density (e.g., denser than the density medium but less dense than the particle; denser than the sample but less dense than the density medium; or denser than the sample but less dense than the particle). The separation layer fluid can include any useful substance, e.g., a hydrophobic material, a mineral oil, an organic oil, a charged or water ordering polymer, a salt in a water-based medium, a fluoroalkane fluid, a perfluorocarbon, or a perfluoroalkane fluid. Further details on separation layer fluids are provided in U.S. Pat. Nos. 8,962,346 and 9,304,129, each of which is incorporated herein by reference in its entirety.

Label Agents and Capture Agents

A label agent includes any moiety that can emit a signal suitable for detection, such as an optical or an electrical signal. Exemplary moieties can include a fluorescent moiety (e.g., a fluorophore), a probe (e.g., any described herein), or a label (e.g., a fluorescent, chemiluminescent, or electroactive label, such as any described herein).

The label agent can optionally include a capture portion, which binds to a target or a portion thereof. Furthermore, a label agent can be used in conjunction with a capture agent (e.g., as in a sandwich assay, which can include use of a capture agent to bind a first region of the target to a bead and use of a label agent to bind to a second region of the target in order to provide a detectable signal).

Exemplary capture agents include a protein that binds to or detects one or more markers (e.g., an antibody or an enzyme), an affibody, an aptamer, a globulin protein (e.g., bovine serum albumin), a nanoparticle, a microparticle, a sandwich assay reagent, a nucleic acid (e.g., single stranded nucleic acid, double stranded nucleic acid, hairpin nucleic acid, DNA, RNA, cell-free nucleic acids, as well as chimeras thereof, hybrids thereof, or modifications thereof), a toxin capture agent (e.g., a sarcin-ricin loop capture agent), a major histocompatibility complex capture agent (e.g., a WIC II capture agent), or a catalyst (e.g., that reacts with one or more markers.

Exemplary label agents include a capture agent (e.g., any herein), a detectable molecule or compound (e.g., a probe (e.g., a fluorescence resonance energy transfer or FRET probe, a fluorescent probe, and/or a quencher probe), an electroactive label, an electrocatalytic label, a fluorescent label, a colorimetric label, a quantum dot, a particle, a nanoparticle, a microparticle, a barcode, a radio label (e.g., an RF label or barcode), avidin, biotin, a tag, a dye, a marker, an enzyme that can optionally include one or more linking agents and/or one or more dyes, etc.), or a combination of a capture agent with a detectable molecule or a detectable compound. Other exemplary label agents include nucleic acid dyes, lipid dyes, etc.

Other Reagents

The present device can be configured for use with any number of reagents either on-chip and/or off-chip. Exemplary reagents include a lysing agent (e.g., a detergent, such as saponin); a sterilization agent (e.g., a bleach, such as sodium hypochlorite or calcium hypochlorite; an oxidizer, such as chlorine dioxide, sodium dichloroisocyanurate, a peroxide, ethylene oxide, ozone gas, peracetic acid, hypochlorous acid, etc.; a surfactant, such as a cationic, anionic, nonionic, or zwitterionic surfactants, as well as combinations thereof; an antibiotic; a catalyst; an enzyme; a phage, e.g., a bacteriophage; a disinfectant, such as glutaraldehyde, stabilized hydrogen peroxide, peracetic acid, or formaldehyde; a biocide; an antiseptic; a detergent; a deodorant; and combinations thereof, where the sterilization agent can be in gas, liquid, semi-solid, or solid form, such as a powder, pellet, granule, gel, lyophilized, or freeze-dried forms), a detection agent (e.g., a dye, such as an electroactive detection agent, a fluorescent dye, a luminescent dye, a chemiluminescent dye, a colorimetric dye, a radioactive agent, etc.; a particle, such as a microparticle, a nanoparticle, a latex bead, a colloidal particle, a magnetic particle, a fluorescent particle, a coated particle, etc.), a label (e.g., an electroactive label, an electrocatalytic label, a fluorescent label, a colorimetric label, a quantum dot, a nanoparticle, a microparticle, a barcode, a radio label (e.g., an RF label or barcode), avidin, biotin, a tag, a dye, a marker, an enzyme that can optionally include one or more linking agents and/or one or more dyes), an amplifying agent (e.g., a PCR agent, such as a polymerase, one or more deoxyribonucleotide triphosphates, a divalent metal (e.g., $MgCl_2$), a template DNA, a primer (e.g., for binding to a selective region of the target nucleic acid)), a capture agent (e.g., such as a protein that binds to or detects one or more markers (e.g., an antibody or an enzyme), a globulin protein (e.g., bovine serum albumin), a nanoparticle, a microparticle, a sandwich assay reagent, a catalyst (e.g., that reacts with one or more markers), an enzyme (e.g., that reacts with one or more markers, such as any described herein)), a buffer (e.g., a phosphate or borate buffer, which can optionally include one or more salts, kosmotropes, and/or chaotropes), an alcohol (e.g., from about 1% v/v to about 10% v/v methanol, ethanol, or isopropanol), a preservative (e.g., sucrose or trehalose), a blocking agent (e.g., gelatin, casein, bovine serum albumin, IgG, PVP, or PVA), a bead (e.g., a glass bead, silica bead, etc., such as to aid in mixing), etc., as well as combinations thereof.

Samples

The sample can include any useful targets. Exemplary targets include cells (e.g., white blood cells, red blood cells, neutrophils, lymphocytes, monocytes, granulocytes, tumor cells, etc.), viruses, bacteria, and/or complexes. In any sample, a panel of targets can be present (e.g., a plurality of bacteria, pathogen(s), etc.).

Exemplary targets include a bacterium, such as such as *Bacillus* (e.g., *B. anthracis*), Enterobacteriaceae (e.g., *Salmonella*, *Escherichia coli*, *Yersinia pestis*, *Klebsiella*, and *Shigella*), *Yersinia* (e.g., *Y. pestis* or *Y. enterocolitica*), *Staphylococcus* (e.g., *S. aureus*), *Streptococcus*, *Gonorrheae*, *Enterococcus* (e.g., *E. faecalis*), *Listeria* (e.g., *L. monocytogenes*), *Brucella* (e.g., *B. abortus*, *B. melitensis*, or *B. suis*), *Vibrio* (e.g., *V. cholerae*), *Corynebacterium diphtheria*, *Pseudomonas* (e.g., *P. pseudomallei* or *P. aeruginosa*), *Burkholderia* (e.g., *B. mallei* or *B. pseudomallei*), *Shigella* (e.g., *S. dysenteriae*), *Rickettsia* (e.g., *R. rickettsii*, *R. prowazekii*, or *R. typhi*), *Francisella tularensis*, *Chlamydia psittaci*, *Coxiella burnetii*, *Mycoplasma* (e.g., *M. mycoides*), etc.; an allergen, such as peanut dust, mycotoxins, mold spores, or bacterial spores such as *Clostridium botulinum* and *C. perfringens*; a toxin, such as ricin, mycotoxin, tetrodotoxin, anthrax toxin, botulinum toxin, staphylococcal enterotoxin B, or saxitoxin; a virus, such as Adenoviridae (e.g., adenovirus), Arenaviridae (e.g., Machupo virus), Bunyaviridae (e.g., Hantavirus or Rift Valley fever virus), Coronaviridae, Orthomyxoviridae (e.g., influenza viruses), Filoviridae (e.g., Ebola virus and Marburg virus), Flaviviridae (e.g., Japanese encephalitis virus and Yellow fever virus), Hepadnaviridae (e.g., hepatitis B virus), Herpesviridae (e.g., herpes simplex viruses), Papovaviridae (e.g., papilloma viruses), Paramyxoviridae (e.g., respiratory syncytial virus, measles virus, mumps virus, or parainfluenza virus), Parvoviridae, Picornaviridae (e.g., polioviruses), Poxviridae (e.g., variola viruses), Reoviridae (e.g., rotaviruses), Retroviridae (e.g., human T cell lymphotropic viruses (HTLV) and human immunodeficiency viruses (HIV)), Rhabdoviridae (e.g., rabies virus), and Togaviridae (e.g., encephalitis viruses, yellow fever virus, and rubella virus)); a protozoon, such as *Cryptosporidium parvum*, *Encephalitozoa*, *Plasmodium*, *Toxoplasma gondii*, *Acanthamoeba*, *Entamoeba histolytica*, *Giardia lamblia*, *Trichomonas vaginalis*, *Leishmania*, or *Trypanosoma* (e.g., *T. brucei* and *T. cruzi*); a helminth, such as cestodes (tapeworms), trematodes (flukes), or nematodes (roundworms, e.g., *Ascaris lumbricoides*, *Trichuris trichiura*, *Necator americanus*, or *Ancylostoma duodenale*); a parasite (e.g., any protozoa or helminths described herein); a fungus, such as Aspergilli, Candidae, *Coccidioides immitis*, and Cryptococci; a pathogen; an environmental contaminant; a water additive; an agricultural marker; a nucleic acid (e.g., oligonucleotides, polynucleotides, nucleotides, nucleosides, molecules of DNA, or molecules of RNA, including a chromosome, a plasmid, a viral genome, a primer, or a gene); a genetic modification (e.g., antibiotic resistance marker gene); a protein (e.g., a glycoprotein, a metalloprotein, an enzyme, a prion, or an immunoglobulin); a metabolite; a sugar; a lipid; a lipopolysaccharide; a salt; or an ion. Targets also include food-borne pathogens, such as *Salmonella* (e.g., *Salmonella Typhimurium*), pathogenic *E. coli* (e.g., O157: H7), *Bacillus* (e.g., *B. cereus*), *Clostridium botulinum, Listeria monocytogenes, Yersinia* (e.g., *Y. enterocolitica*), Norovirus (e.g., Norwalk virus), *Shigella, Staphylococcus aureus, Toxoplasma gondii, Vibrio* (e.g., *V. vulnificus, V. cholera, V. parahaemolyticus*), *Campylobacter jejuni*, and *Clostridium perfringens*; and weaponized pathogens, such as *Bacillus anthracis, Yersinia pestis, Francisella tularensis, Brucella* (e.g., *B. suis*), *Burkholderia mallei, Burkholderia pseudomallei, Shigella, Clostridium botulinum, Variola* (e.g., *V. major*), Filoviridae (e.g., Ebola virus and Marburg virus), Arenaviridae (e.g., Lassa virus and Machupo virus), *Clostridium perfringens*, any food-borne pathogen (e.g., *Salmonella* species, *Escherichia coli* O157:H7, or *Shigella*), *Chlamydia psittaci, Coxiella burnetii, Staphylococcal aureus, Rickettsia* (e.g., *R. prowazekii* or *R. rickettsii*), Alphavirus (e.g., Venezuelan equine encephalitis virus, eastern equine encephalitis virus, or western equine encephalitis virus), *Vibrio cholerae, Cryptosporidium parvum*, Henipavirus (e.g., Nipah virus), Bunyaviridae (e.g., Hantavirus or Rift Valley fever virus), Flaviviridae (e.g., Japanese encephalitis virus and Yellow fever virus), and *Coccidioides* spp.

In some instances, the sample includes any useful test sample. The test sample can include any useful sample, such as a microorganism, a virus, a bacterium (e.g., enteric bacterium), a fungus, a parasite, a helminth, a protozoon, a cell (e.g., a cell culture), tissue (e.g., tissue homogenates), a fluid, a swab, a biological sample (e.g., blood, such as whole blood, serum, plasma, saliva, urine, cerebral spin fluid, etc.), a buffer, a plant, an environmental sample (e.g., air, soil, and/or water), etc. The test sample can also include a plurality of targets. The sample can be optionally processed (e.g., on-chip or off-chip) in any useful manner (e.g., before or after transporting to the assay area, or even within the assay area), e.g., diluted, mixed, homogenized, lysed, sterilized, incubated, labeled, etc.

Methods

The microfluidic devices and systems herein can be adapted for any useful diagnostic technique. Exemplary diagnostic techniques include particle quantification (e.g., cell counting, differential white blood cell count), sedimentation assays, sandwich assay, nucleic acid assays, agglutination assays, toxin assays, amplification assays, etc.

In one non-limiting instance, the devices and systems herein are adapted to perform a method of conducting a sandwich assay. One exemplary method can include: providing a fluid sample in a channel on a microfluidic device (e.g., a microfluidic disc), the fluid sample including a plurality of particles (e.g., beads) having complexes formed thereon, individual ones of the complexes including a capture agent, a target (e.g., a target analyte), and a label agent, the fluid sample further including a free label agent; providing a density medium from a media reservoir to an assay area (e.g., a detection region) of the microfluidic device by applying a first centrifugal force, the media reservoir on the microfluidic disc and in fluid communication with the assay area, the assay area fluidly coupled to the channel, where the density media has a density within a range, an upper bound of the range being lower than a density of the plurality of particles and a lower bound of the range being higher than a density of the fluid sample; transporting the plurality of particles including the complexes through the density media, where the free label agent is restricted from transport through the density media, and where a first plurality of particles having a first property is transported to a first distinct detection location in the assay area and a second plurality of beads having a second property different than the first property is transported to a second distinct detection location in the assay area; detecting a signal from the label agents of the complexes; and generating an electronic detection signal based, at least in part, on the signal detected from the label agents. The method can optionally include, prior to the transporting step, spinning the microfluidic device to apply a second centrifugal force on the plurality of particles, the first and second centrifugal forces being different.

In another non-limiting instance, the devices and systems herein are adapted to perform a method of conducting an assay (e.g., a sedimentation assay). An exemplary method can include: layering a mixture on a density medium in an assay area, where the mixture includes a sample, a first separation layer fluid, and a plurality of sedimentation particles, where the sedimentation particles have a density greater than the density medium, and where the layering a mixture includes forming, with the first separation layer fluid, an interface between the density medium and the sample, between the sample and the sedimentation particles, or between the density medium and the sedimentation particles; subjecting the mixture to a sedimentation force such that the sedimentation particles, if formed, travel through the first separation layer fluid and the density medium to a detection area; and detecting a presence of an analyte of interest in the detection area. Other exemplary assays (e.g., sandwich assays and sedimentation assays) are described in U.S. Pat. Nos. 8,945,914 and 8,962,346, each of which is incorporated herein by reference in its entirety.

In yet another non-limiting instance, the devices and systems herein are adapted to perform a method of conducting an agglutination assay. An exemplary method can include: layering a mixture on a density medium, where the mixture includes a sample and a first population of coated particles (e.g., coated beads) having a first density, where the first population includes a capture agent (e.g., an affinity reagent) for a target (e.g., an analyte of interest), where the first population is configured to form aggregates with the target when present, where the density medium has a minimum density greater than the first density; subjecting the mixture to a sedimentation force such that the aggregates, if formed, travel through the density medium; and detecting a presence of the aggregates in an assay area (e.g., a detection area or a detection region). Other exemplary agglutination assays are described in U.S. Pat. No. 9,244,065, which is incorporated herein by reference in its entirety.

In another non-limiting instance, the devices and systems herein are adapted to perform a method of conducting a toxin activity assay. An exemplary method can include: generating a plurality of complexes on a plurality of particles (e.g., beads) by action of an active toxin in a fluid sample, individual complexes of the plurality of complexes including a capture agent and a label agent; transporting the plurality of particles including the complexes through a density medium, where the density medium has a density lower than a density of the particles and higher than a density of the fluid sample, and where the transporting occurs, at least in part, by sedimentation; and detecting a signal from the label agents of the plurality of complexes bound to the plurality of particles. Other exemplary toxin activity assays are described in U.S. Pat. No. 9,304,128, which is incorporated herein by reference in its entirety.

In yet another non-limiting instance, the devices and systems herein are adapted to perform a method of conducting a metabolite test. An exemplary system can include: a chamber that includes a fluid, and is configured to accept a sample fluid, where the sample fluid includes a delta-9-THC compound and a metabolite (e.g., a cocaine-based compound, a methamphetamine-based compound, a methamphetamine compound, an amphetamine compound, an opiate-based compound, an MDMA-based compound, a ketamine-based compound, a PCP-based compound, a lysergic acid diethylamide-based compound, or a psilocybin-based compound); and a detection module that, responsive to a centrifugal force being applied to the fluid and the sample fluid, outputs an indication of a level of the delta-9-THC compound and/or the metabolite in the sample fluid.

An exemplary method can include: exposing an agent (e.g., a capture agent, a label agent, or a combination thereof, such as a fluorophore-labelled analyte specific antibody) to a first fluid including at least one of: a free analyte, where the free analyte, if present in the first fluid, originates from a test sample added to the first fluid; or a bound analyte, where the bound analyte, if present in the first fluid, is attached to a first particle having a first density, the agent has a stronger binding affinity for the free analyte than for the bound analyte, the first fluid is in a chamber, the chamber has an open end and a closed end and further includes a second liquid, the second liquid is located at the closed end of the chamber and the first liquid is located between the second liquid and the open end of the chamber; applying a centrifugal force to the chamber, wherein the first particle transfers from the first liquid to the second liquid; irradiating the second liquid to generate a detectable signal in the second liquid (e.g., with light energy to generate fluorescence in the second liquid); and quantifying an amount of free analyte in the second liquid based upon a magnitude of the detectable signal at the second liquid, where the quantification is based upon a threshold value. In some embodiments, the second liquid includes a colloidal suspension of silicon nanoparticles, dextran, poly(ethylene glycol), glycerol, sorbitol, iodixanol, cesium chloride, or perfluorodecalin.

Materials

The present devices and systems can be formed from any useful material. Exemplary materials include a polymer, such as polymethyl methacrylate (PMMA), polyethylene terephthalate (PET, e.g., biaxially-oriented PET or bo-PET), an acrylic polymer, poly(dimethylsiloxane) (PDMS), polycarbonate (PC), cyclo-olefin copolymer (COC), polyethylene terephthalate glycol (PETG), polyethylene (PE, such as branched homo-polymer PE), polyvinylchloride (PVC), polystyrene (PS), styrene copolymer, polyimide (PI), polypropylene (PP), polytetrafluoroethylene (PTFE), polynorbornene (PN), poly(4-methyl-1-pentene), silicone, and combinations or co-polymers thereof; silicon; glass; quartz; fused silica; an adhesive, such as any described herein; as well as combinations thereof (e.g., combinations of such materials provided in separate layers or within the same layer). Polymers can include any useful additive, such as, e.g., fillers (e.g., mica, talc, or calcium carbonate), plasticizers (e.g., dioctyl phthalate), heat stabilizers (e.g., organotin compounds), antioxidants (e.g., phenols or amines), and/or UV stabilizers (e.g., benzophenones or salicylates). Such materials can be provided in any useful form, such as in one or more layers that can be laminated to provide the assembled cartridge; and fabricated in any useful manner, such as by way of embossing, etching, injection molding, surface treatments, photolithography, bonding and other techniques.

EXAMPLES

Example 1: Non-Contact Temperature Control System

In an effort to expand the versatility of a rotating microfluidic system by enabling nucleic acid tests with techniques such as loop-mediated isothermal amplification (LAMP), a non-contact heating system was integrated into the platform. An infrared emitter was used to heat aqueous samples and maintain a stable, uniform temperature, e.g. 65° C. to conduct the LAMP reaction. This approach avoids the complexity and cost of incorporating both auxiliary on-disc hardware and a slip-ring for electrically interfacing with the rotating disc (see, e.g., Martinez-Duarte R et al., "The integration of 3D carbon-electrode dielectrophoresis on a CD-like centrifugal microfluidic platform," *Lab Chip* 2010; 10:1030-43; and Abi-Samra K et al., "Electrochemical velocimetry on centrifugal microfluidic platforms," *Lab Chip* 2013; 13:3253-60).

Established heating methods for centrifugal platforms include induction heating (see, e.g., Chen X et al., "Wirelessly adaptable heater array for centrifugal microfluidics and *Escherichia Coli* sterilization," $35^{th}$ *Ann. Int. Conf. IEEE EMBS*, 3-7 Jul. 2013 in Osaka, Japan, pp. 5505-8), which offers a non-contact solution but requires complex circuitry and on-disc electrodes. Infrared laser heating has been used successfully but suffers from inefficiency and added disc complexity by requiring an embedded metal plate to achieve indirect heating of the sample (see, e.g., Kim T H et al., "Fully integrated lab-on-a-disc for nucleic acid analysis of food-borne pathogens," *Anal. Chem.* 2014; 86:3841-8). Thermoelectric heating, commonly used for PCR thermocyclers, has been implemented but requires additional moving parts, such as a linear actuator (see, e.g., Amasia M et al., "Centrifugal microfluidic platform for rapid PCR amplification using integrated thermoelectric heating and ice-valving," *Sens. Actuat. B* 2012; 161:1191-7) or a vacuum pressure system (see, e.g., Roy E et al., "From cellular lysis to microarray detection, an integrated thermoplastic elastomer (TPE) point of care lab on a disc," *Lab Chip* 2015; 15:406-16), to bring the disc into contact with the heating element. In addition, this must be performed on a stationary disc, making real-time detection more difficult.

Herein, we provide a method for uniformly heating an array of biological samples on a centrifugal microfluidic device using an infrared emitter, accurately achieving temperatures required for diagnostic techniques such as isothermal amplification. In particular, we developed an inexpensive non-contact heating system making use of a carbon filament, medium wave infrared emitter that outputs peak wavelengths in the micron range (e.g., of from about 2.4 to about 2.7 μm) that irradiates a PMMA microfluidic disc during slow (e.g., 100 RPM) rotation.

Figure 4A:
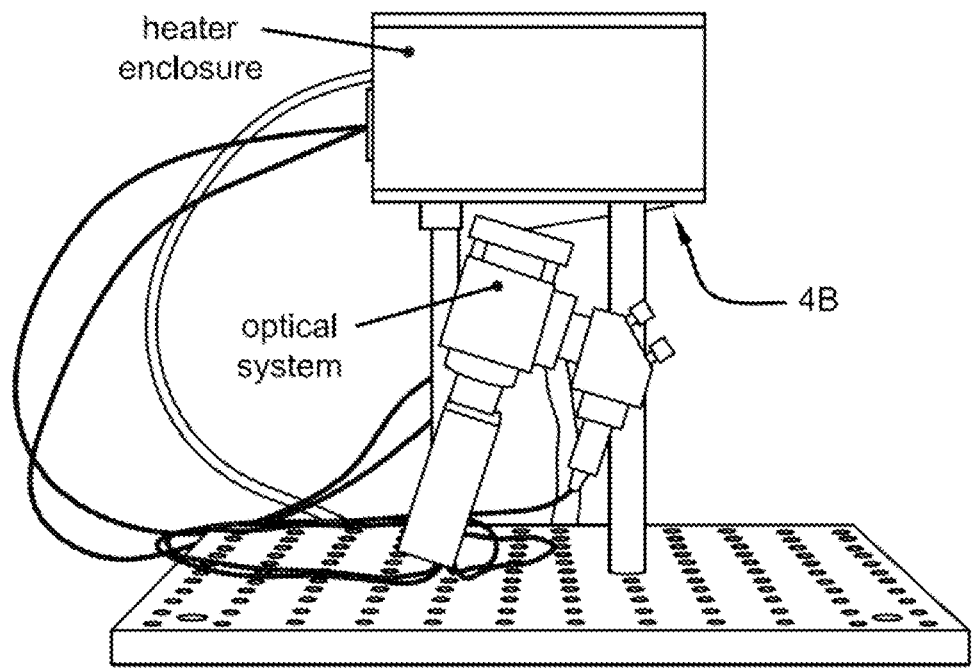
FIG. 4A-4D shows a prototype system including an exemplary non-contact temperature control system mounted over an optical detection module configured for laser-induced fluorescence. Provided are photographs of the system (FIG. 4A) including a medium wave infrared emitter and a cooling fan (FIG. 4B). Also provided is an illustration of an exemplary, fully integrated prototype having the heater enclosure hinged over the microfluidic disc, which was mounted to a lower enclosure containing the motor drive, optical system, and control electronics (FIG. 4C), as well as a simplified illustration of the heating system showing the position of the heater over the rotating disc when in operation and the option of a mask for selective heating when combining assays with different temperature requirements (FIG. 4D).
Figure 4B:
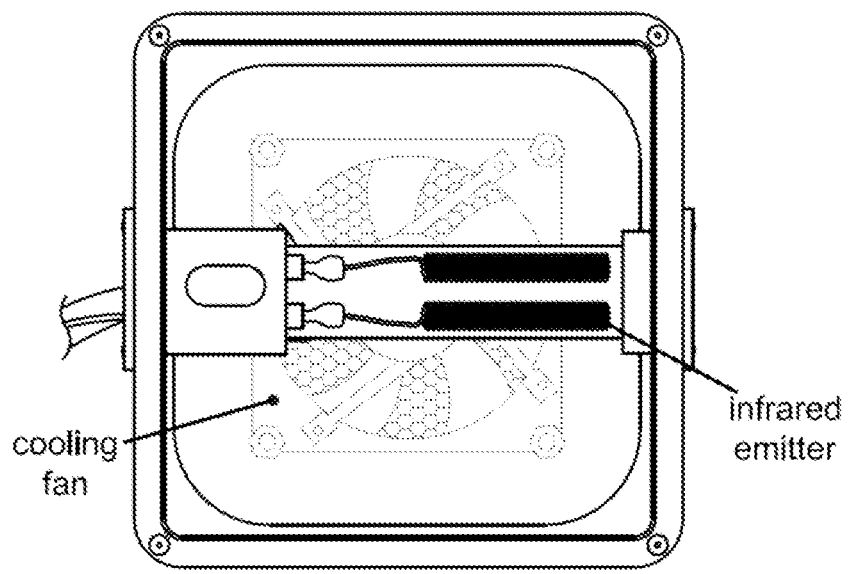

The temperature control system was integrated into an upper enclosure (e.g., the lid) of the instrument in order to heat the disc from above, which avoids exposing sensitive optical and electrical components in the lower enclosure (e.g., the base of the platform) to waste heat. A non-limiting prototype was built around a 3D-printed shell (FIG. 4A) that houses an axial cooling fan and an infrared emitter (FIG. 4B).

The emitter was a custom 100 W medium wave, carbon filament infrared emitter (from Heraeus Noblelight Ltd., Hanau, Germany), which was powered by a 12 VDC source to ensure compatibility with battery power. The emitter had peak wavelengths at about 2.4-2.7 µm and featured a dual-filament design with a gold retro-reflector to focus radiation into a roughly 50 mm by 20 mm region. This focal spot was aligned along a radial section of the microfluidic disc, centered with the assay area (e.g., a reaction chamber). The medium wave radiation band emitted by the heater closely matched the peak absorption wavelengths of water, enabling efficient heating of the low-volume (e.g., 10 µL) aqueous samples contained in the disc.

In some instances, prior to heating the disc, an adhesive backed foil layer was applied over the center of the disc (e.g., over the sample ports) to prevent heating of the sealing barrier, which can cause leakage. With the disc mounted on the motor hub and the lid/heater enclosure closed, the infrared emitter was powered while the disc was spun at low speed (e.g., less than about 300 RPM) to achieve temperature uniformity. In one non-limiting instance, the disc was rotated at 100 RPM, and the heater was powered at 28 W to achieve uniform heating to 65° C. The cooling fan was operated at low speed during heating to minimize heat build-up within the heater enclosure and operated at high speed when the reaction was complete to provide forced convective cooling of the samples.

Figure 4C:
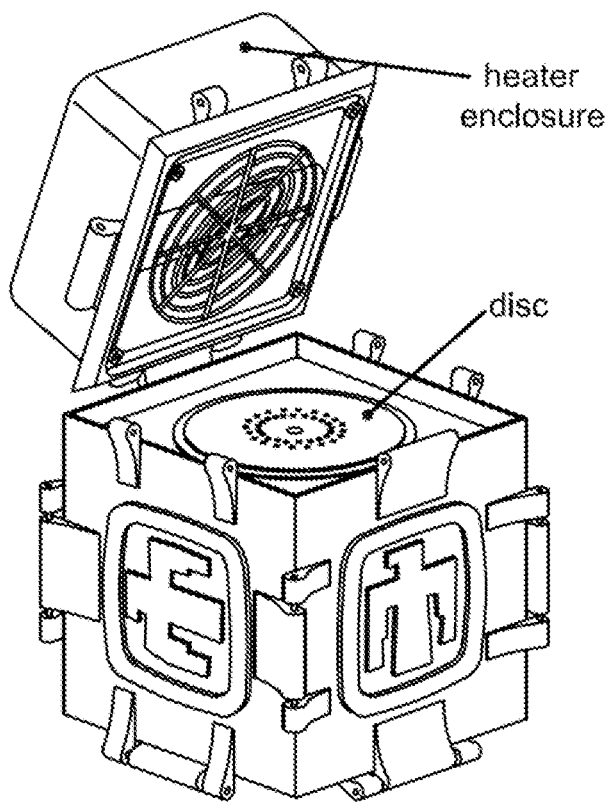
Figure 4D:
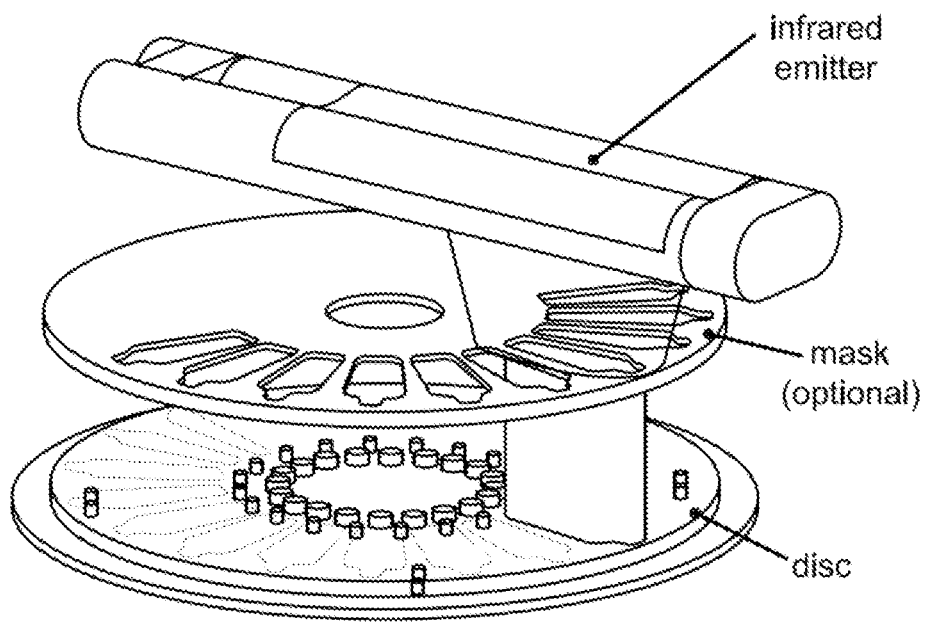
Figure 5A:
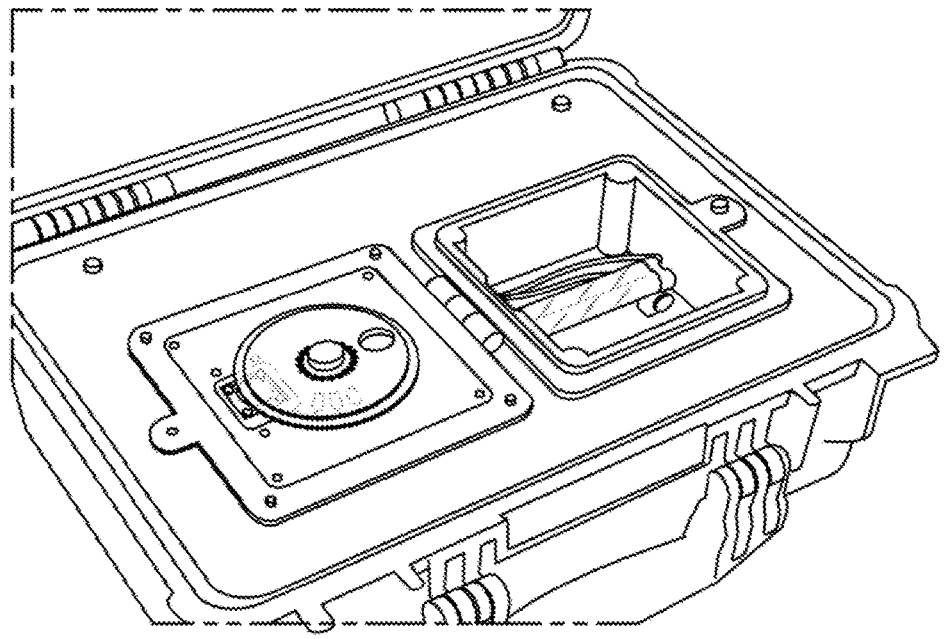
FIG. 5A-5B shows photographs an exemplary system in shown in both the open position (FIG. 5A) and the closed position (FIG. 5B). The heater enclosure can optionally feature a window for observation via infrared camera, and the carbon filament infrared emitter can be seen positioned over the disc when in the closed position.
Figure 5B:
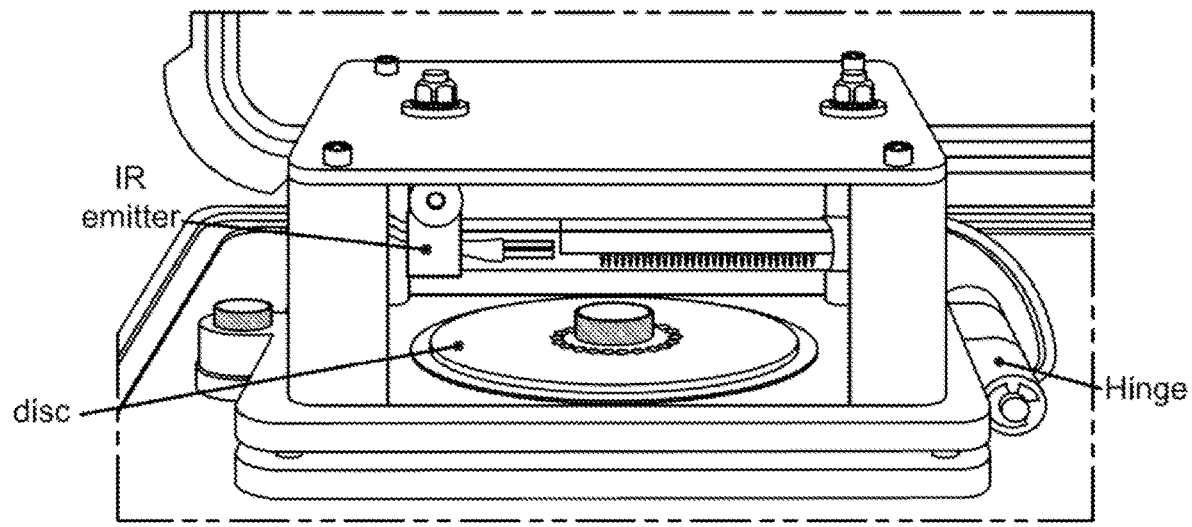

The modules can be integrated into a single system. An exemplary non-contact heating system with a fully enclosed instrument is shown in FIG. 4C, and a simplified rendering of the heating concepts is shown in FIG. 4D. In another embodiment, the non-contact heating system is mounted in a hinged enclosure (FIG. 5A) in order to swivel the heater into position over the disc when ready for operation (FIG. 5B). These modules, along with a power supply and control electronics, can be housed in a Pelican case.

Additional upgrades made to the SpinDx instrumentation included a single brushless servomotor drive system to replace a multi-motor system, which relies on the coordination of a low power brushed DC motor, hobby-grade servo motor, and stepper motor. A single brushless servomotor with a 12-bit absolute encoder (2232S012BX4AES-4096, Dr. Fritz Faulhaber GmbH & Co. KG, Schoenaich, Germany) can provide both the high-speed spin operation for centrifugation through the density medium and precise indexing for the end-point detection step. Optionally, optical switches can be configured to interact with markings on the disc for home positioning.

In addition, a new detection module (e.g., an optical system) can be implemented for compatibility with any useful dye, such as the Syto® 9 fluorescent dye (Thermo Fisher Scientific Inc., Waltham, Mass.), which does not require the sample to be at room temperature for detection, enabling real-time fluorescence monitoring during nucleic acid amplification. The detection module can include a laser diode module, one or more photomultiplier tubes, and excitation and emission filters. This could allow for the termination of a reaction as soon as a detection threshold has been reached, potentially reducing analysis time and power consumption. Other useful modifications can be implemented to enhance and/or simplify device rotation and/or detection.

Efficient, non-contact heating makes available a more complete panel of sensitive diagnostics that require temperature-dependent chemistries without substantially increasing device complexity. This keeps instrument cost low and maintains the viability of a disposable disc. In addition, the benefits of temperature control capabilities extend beyond enabling nucleic acid tests and include enhancement of immunoassay kinetics through heating as well as the ability for the instrument to operate in extreme climates. The platform, which is composed of a compact optical system for laser-induced fluorescence (LIF) detection, a quiet brushless motor, and an efficient non-contact heater, offers an easy-to-use system capable of performing sensitive pathogen screening in a lab-free environment.

Example 2: Temperature Calibration of the Non-Contact Heating System

Calibration of the heating system was performed by first fabricating a disc with a T-type micro-thermocouple (IT-24P, Physitemp Instruments Inc., Clifton, N.J.), which had a 125 µm diameter, embedded in one of the assay areas. This thermocouple was connected to a custom hub with a built-in slip ring, allowing the thermocouple to rotate with the disc while heating while the output wiring remained stationary for voltage measurement. The slip ring output was connected to a linearizing circuit (Omega® TAC80B-T, Omega Engineering, Inc., Stamford, Conn.) that provided a 1 mV/° C. signal, which was collected using data acquisition hardware and LabVIEW. In parallel with the thermocouple measurement, an infrared camera (FLIR T420, FLIR Systems, Inc., Boston, Mass.) was positioned above the disc to measure the top surface temperature of the disc.

Figure 6A:
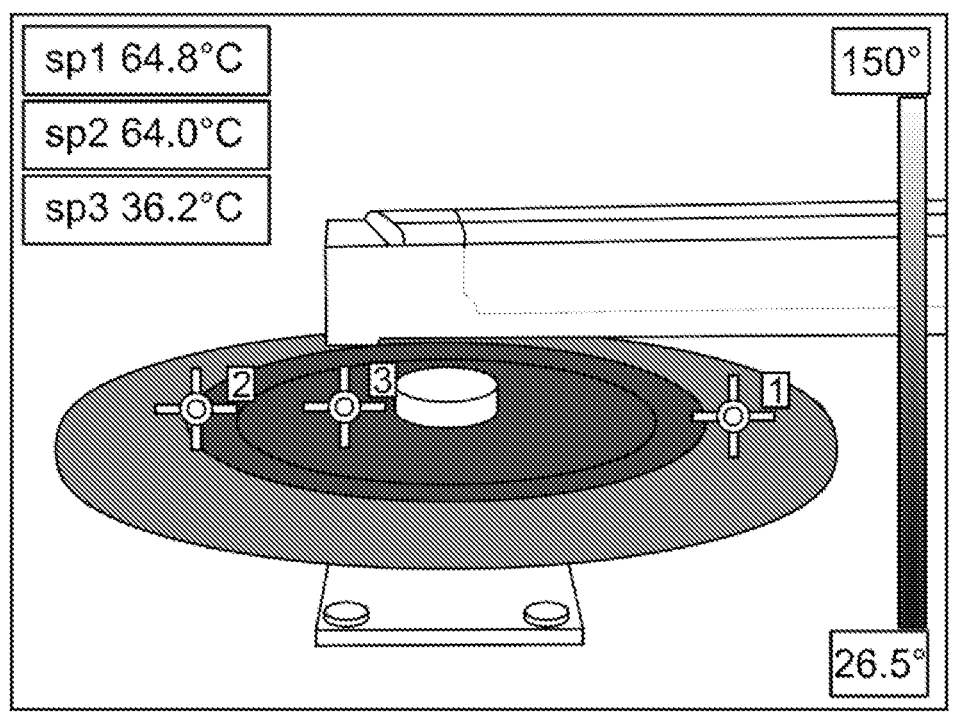
FIG. 6A-6B shows temperature calibration of an exemplary heating system. Provided are a thermal image captured by an infrared camera to monitor disc temperature (FIG. 6A) and a calibration curve generated by correlating surface temperature measurements with sample temperature measurements collected using an embedded micro-thermocouple (FIG. 6B).
Figure 6B:
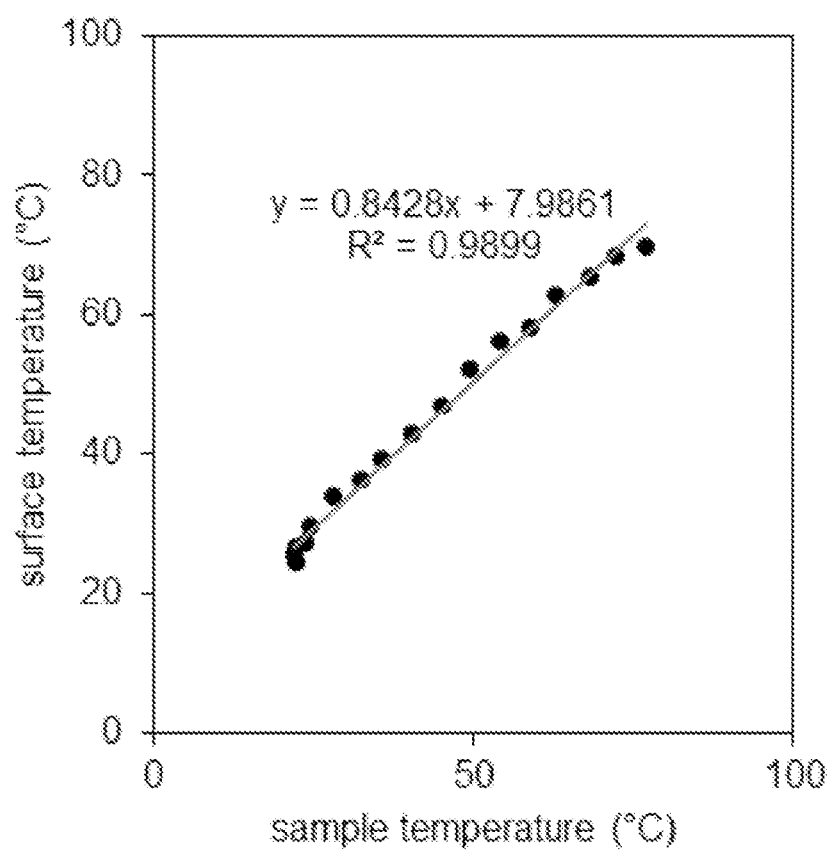

As shown in FIG. 6A, temperature data were collected from the top surface of the disc, namely at location 2 in FIG. 6A, which was directly over the assay areas. Collected data were correlated with true sample temperatures measured using the embedded thermocouple. This correlation, plotted in FIG. 6B, was then used for open loop operation of the disc, requiring only a simple infrared camera measurement to confirm setpoints.

Example 3: On-Chip Amplification and Detection of *E. coli*

Figure 7:
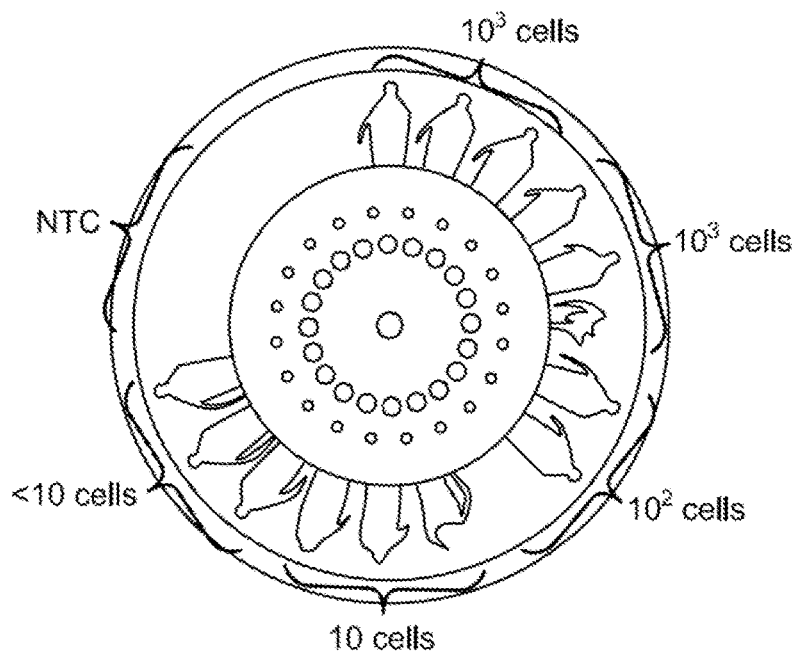
FIG. 7 shows a fluorescence image of a microfluidic disc after successful isothermal amplifications of an E. coli target for a serial dilution from <10 cells/µL to $10^4$ cells/µL performed in triplicate, as compared to a negative control (labeled "NTC").

The calibrated heating system was tested by amplifying a heat-killed *E. coli* O157:H7 target (Cat. No. 50-95-90, KPL, Inc., Gaithersburg, Md.) using a loop-mediated isothermal amplification (LAMP) reaction with QUASR chemistry (see, e.g., Ball C S et al., "Quenching of unincorporated amplification signal reporters in reverse-transcription loop-mediated isothermal amplification enabling bright, single-step, closed-tube, and multiplexed detection of RNA viruses," *Anal. Chem.* 2016; 88:3562-8). In brief, Cy5-labeled primers were employed to target the stx1 gene. With a 10× serial dilution of the target DNA from $10^4$ cells/µL, to ~1 cell/µL, sets of 10 µL reaction were run in triplicate for each template concentration along with a negative template control (NTC). The disc was heated to 65° C., incubated for 45 minutes, and then cooled on ice. Fluorescence was then measured using a gel imager (ProteinSimple, Bio-Techne Corp., Minneapolis, Minn.). Successful detection over the range of dilutions was observed (FIG. 7).

Example 4: Exemplary Portable, Non-Contact Heating System

Figure 8A:
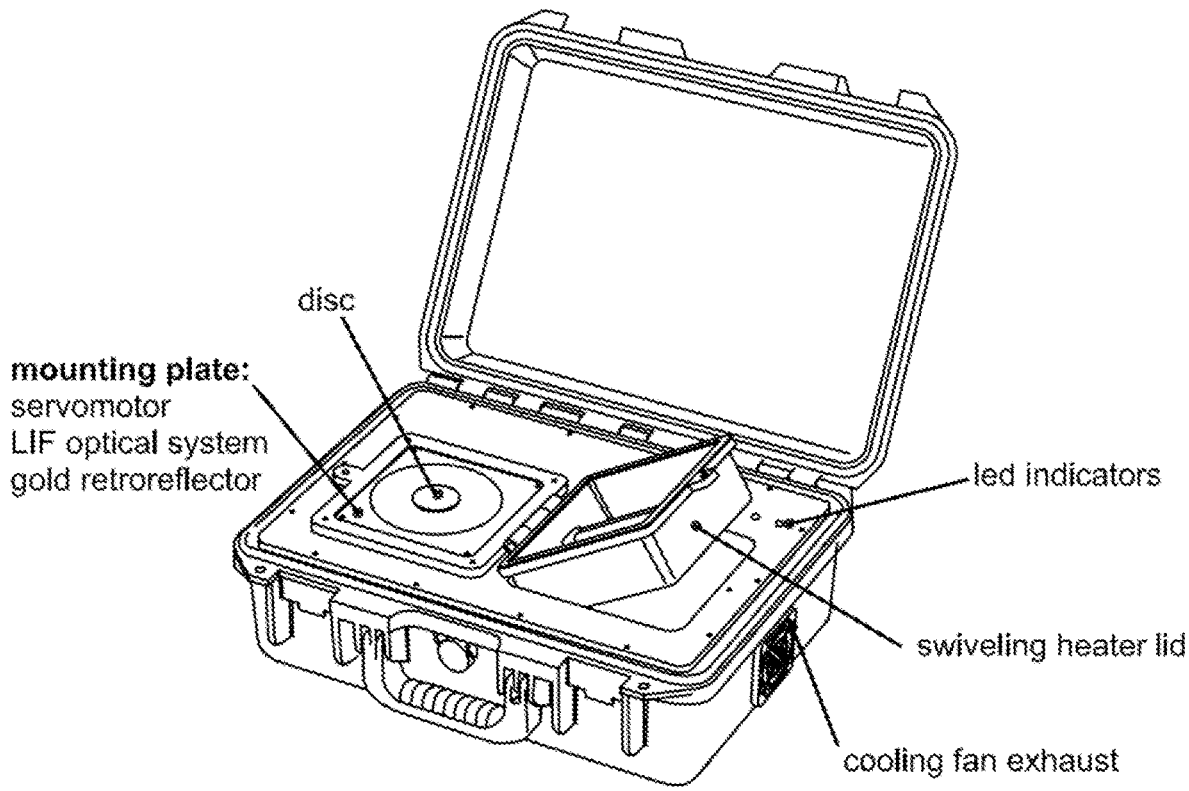
FIG. 8A-8B shows another exemplary portable prototype having a mounting plate configured to support a microfluidic disc and to engage with components of the motor module and the optical detection module. Provided are illustrations of the exemplary, fully integrated prototype in a perspective view (FIG. 8A) and exemplary internal components of the prototype (FIG. 8B).
Figure 8B:
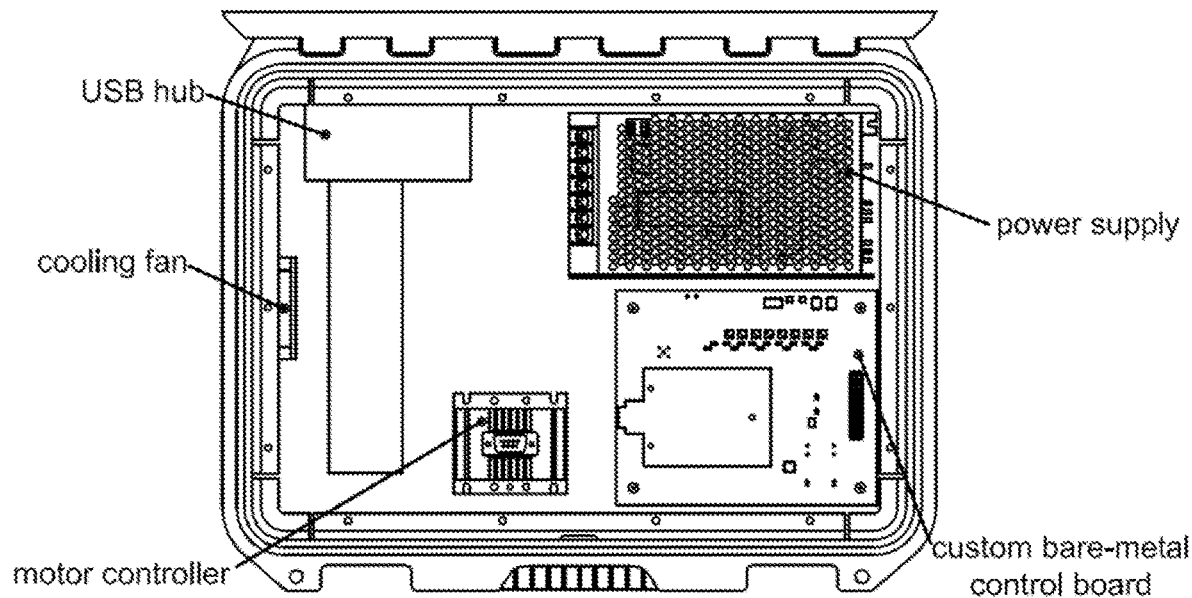

FIG. 8A-8B provides further designs for an exemplary portable, non-contact heating system. The system can include various components incorporated into a single enclosed case.

Figure 9A:
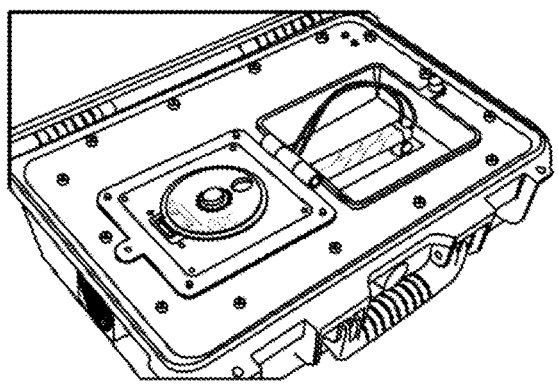
FIG. 9A-9B shows photographs an exemplary system in shown in both the open position (FIG. 9A) and the closed position (FIG. 9B). The position of the heater (e.g., a carbon filament infrared emitter) from the microfluidic disc can be adjusted in any useful manner to provide desired heating extent and location in the closed position.
Figure 9B:
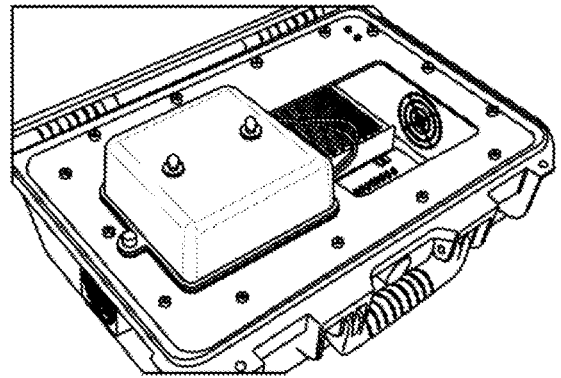
Figure 10A:
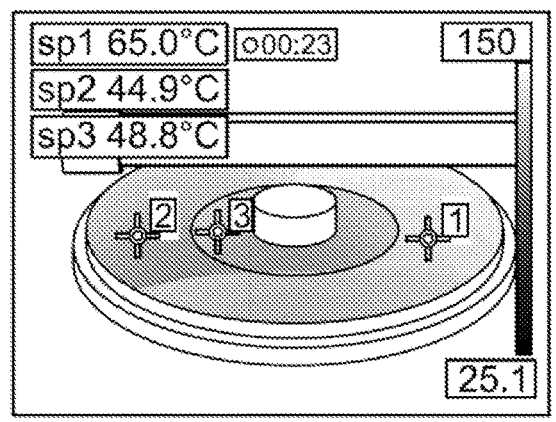
FIG. 10A-10D shows temperature calibration of an exemplary heating system. Provided are time-lapsed thermal images captured by an infrared camera to monitor disc temperature during heating (FIG. 10A), after heating but with an attached reflective mask (FIG. 10B), and after removal of the reflective mask (FIG. 10C-10D).
Figure 10B:
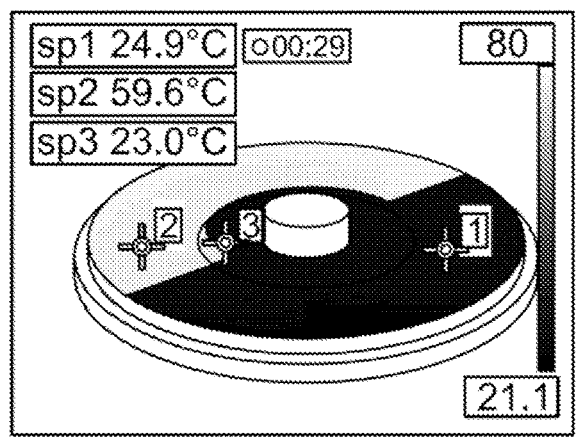
Figure 10C:
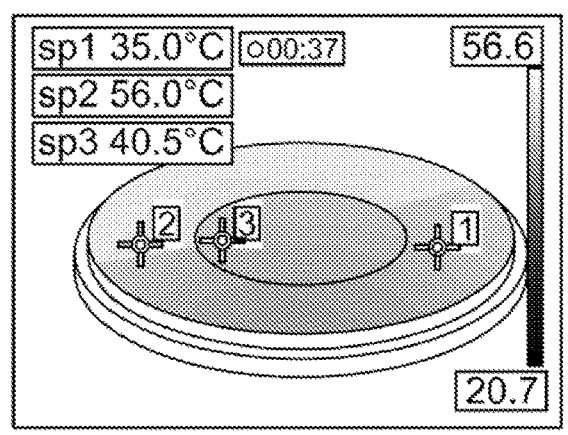
Figure 10D:
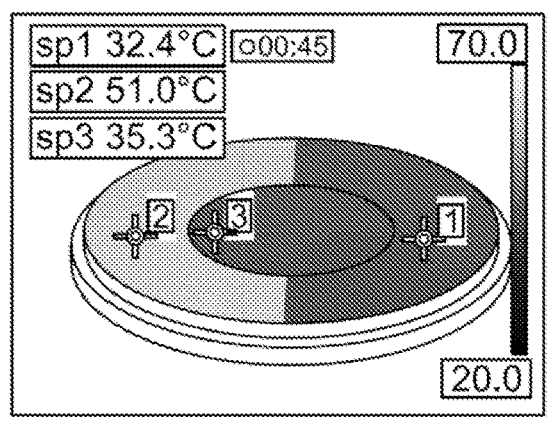

One component can include the non-contact temperature control module, which can be provided as an upper enclosure having the non-contact heater and a lower enclosure having a mounting plate configured to support the microfluidic disc (FIG. 8A). The lower enclosure can further include additional components or modules to rotate the disc and to detect one or more targets (e.g., a servo motor, a reflector, an optical switch, circuitry, and/or a LIF optical system). Provided are photographs of the enclosure in the open position (FIG. 9A, in which the upper and lower enclosures are separated) or in the closed position (FIG. 9B, in which the upper and lower enclosures are in contact).

The system can further include other components and modules. As seen in FIG. 8B, the system can include various components within a lower compartment of the case. This lower compartment underlies the enclosure, which has the non-contact heating temperature control module, the microfluidic device, the motor module, and the detection module. The lower component can include useful components such as an input/output hub (e.g., a USB hub), a cooling fan, a power supply, a control board, and a motor controller.

In some embodiments, a reflective mask was employed to provide different temperature zones. The location of such zones can be controlled by placing a reflective mask in contact with regions of the disc requiring a lower temperature. For instance, a reflective mask can be used to shield immunoassay chambers during heating, achieving two temperature zones: one hotter zone for nucleic acid amplification tests and another cooler zone for immunoassays or any other assay not requiring elevated temperatures.

As seen in FIG. 10A-10D, an elevated temperature zone (e.g., from about 55° C. to 65° C.) can be maintained for microfluidic chambers configured to perform LAMP reactions (e.g., including one or more reagents to conduct LAMP), and a lower temperature zone (e.g., from about 20° C. to 50° C.) for microfluidic chambers configured to perform immunoassays (e.g., including one or more reagents to conduct an immunoassay).

Example 5: Detection of Enteric Bacteria Using On-Chip LAMP Amplification

Figure 11A:
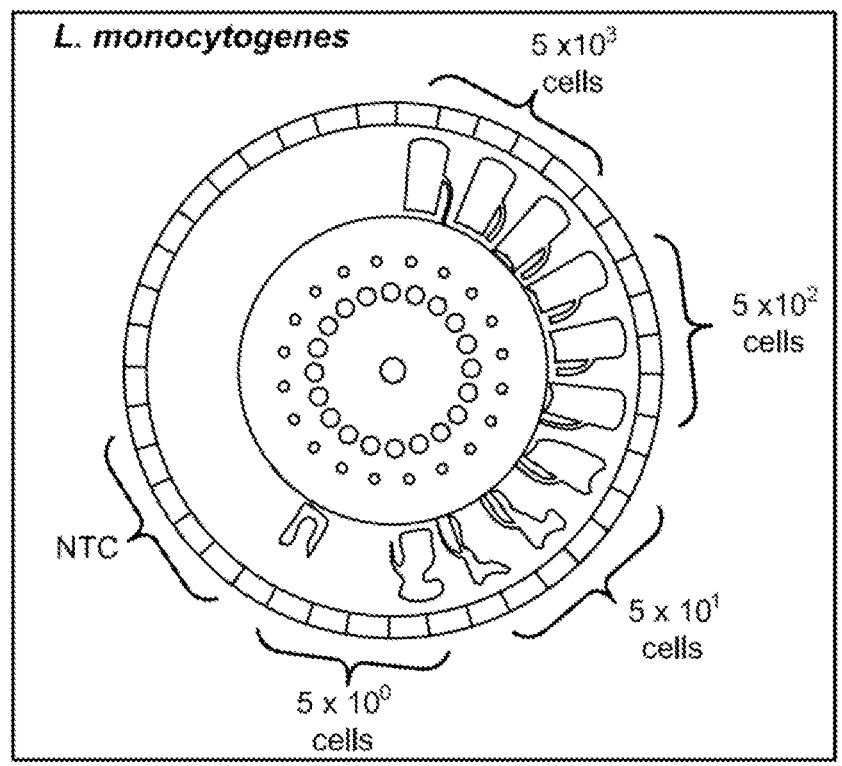
FIG. 11A-11C shows fluorescence images of a microfluidic disc after amplifications of various targets, including L. monocytogenes (FIG. 11A), C. jejuni (FIG. 11B), and E. coli (FIG. 11C) for the provided serial dilutions, as compared to a negative control (labeled "NTC").
Figure 11B:
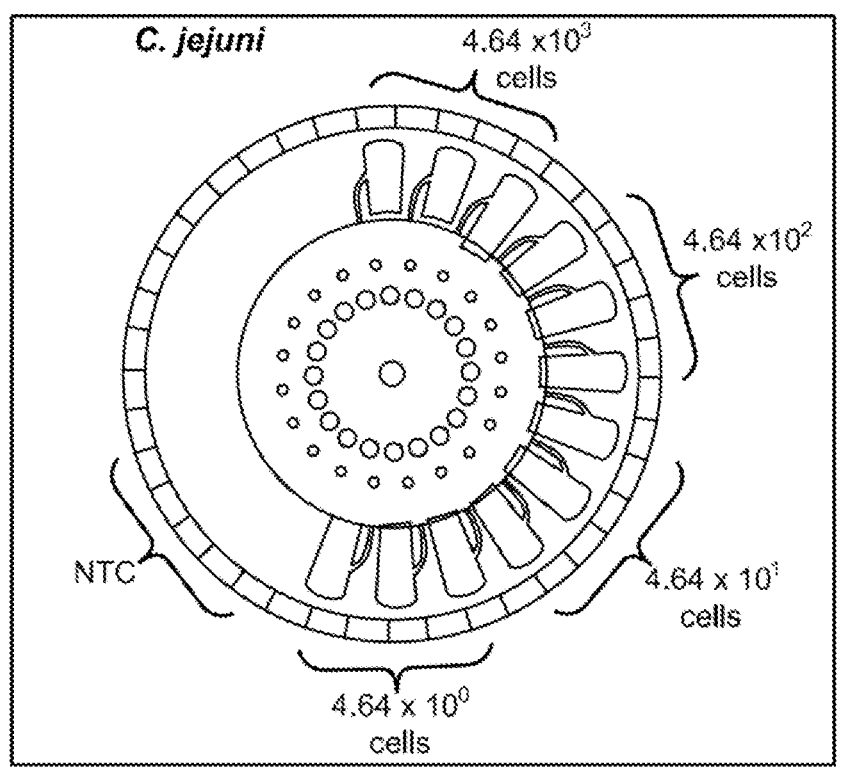
Figure 11C:
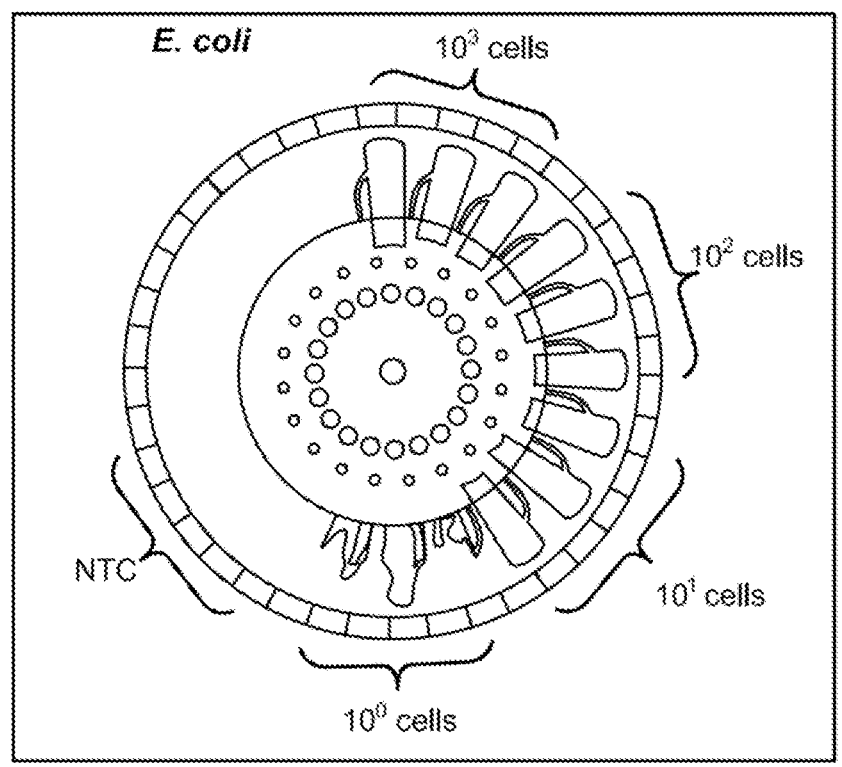
Figure 12A:
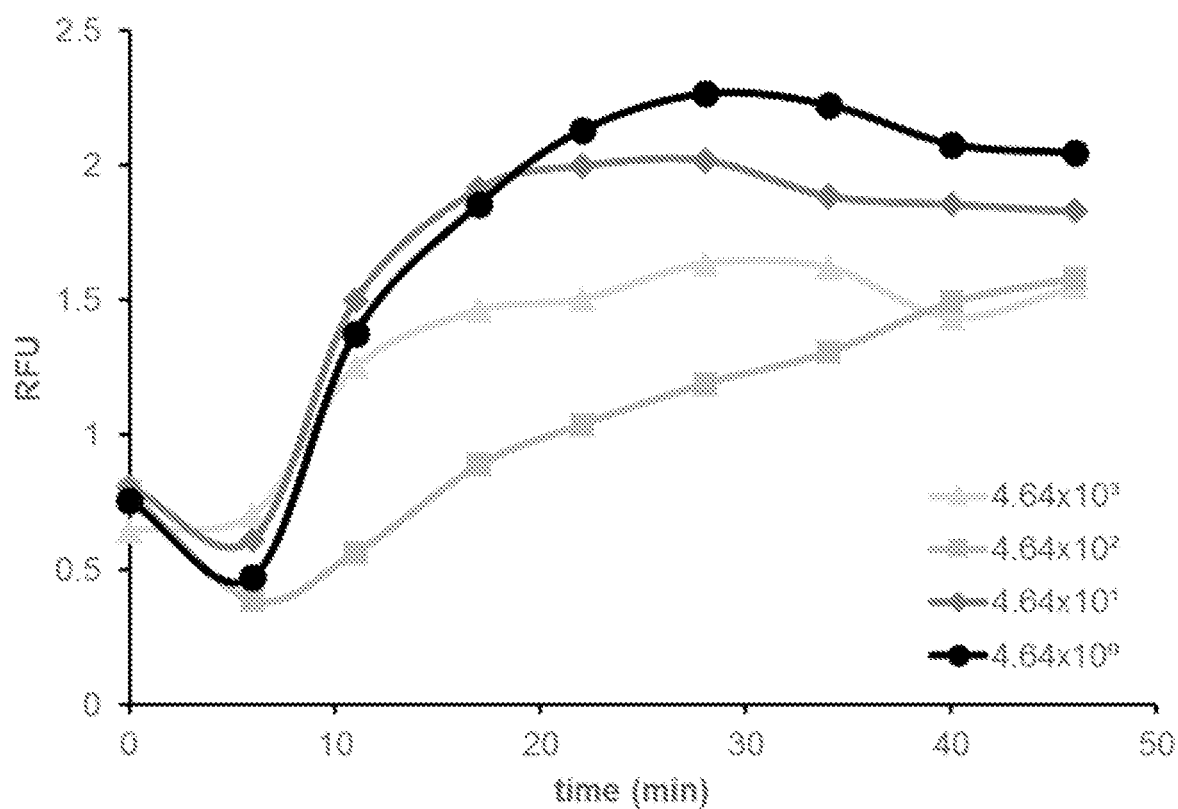
FIG. 12A-12C provides detection of C. jejuni amplification via LAMP using a SYTO® 9 dye. Provided are a graph quantifying real-time fluorescence detection for various serial dilutions of C. jejuni (FIG. 12A), a fluorescence image of microfluidic device after amplification of the target and using a SYTO® 9 dye (FIG. 12B), and another fluorescence image of the same microfluidic device showing confirmation using a secondary Cy5 dye (FIG. 12C).
Figure 12B:
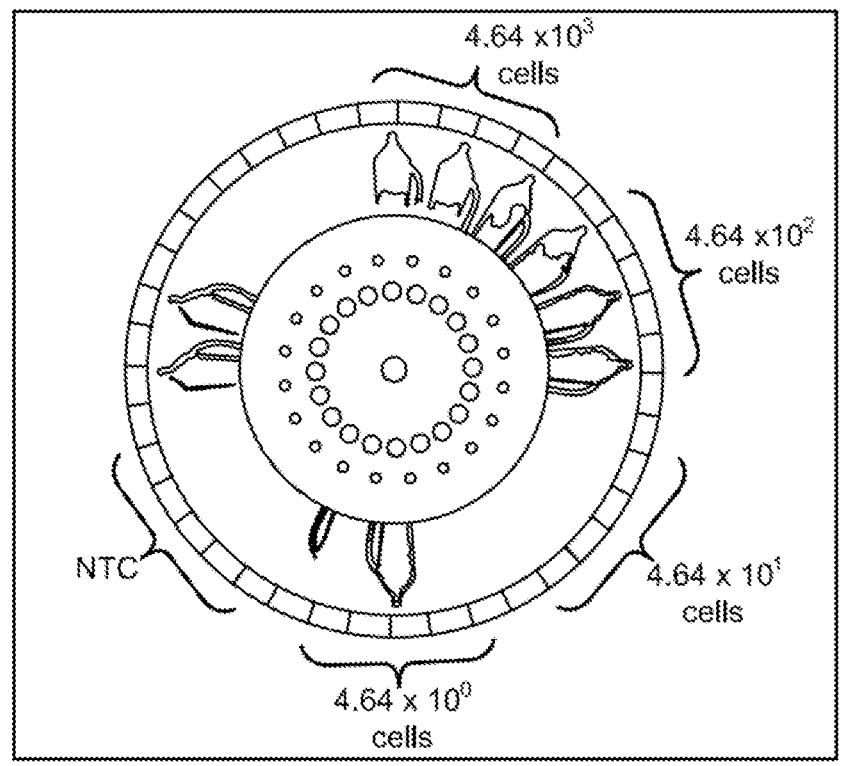
Figure 12C:
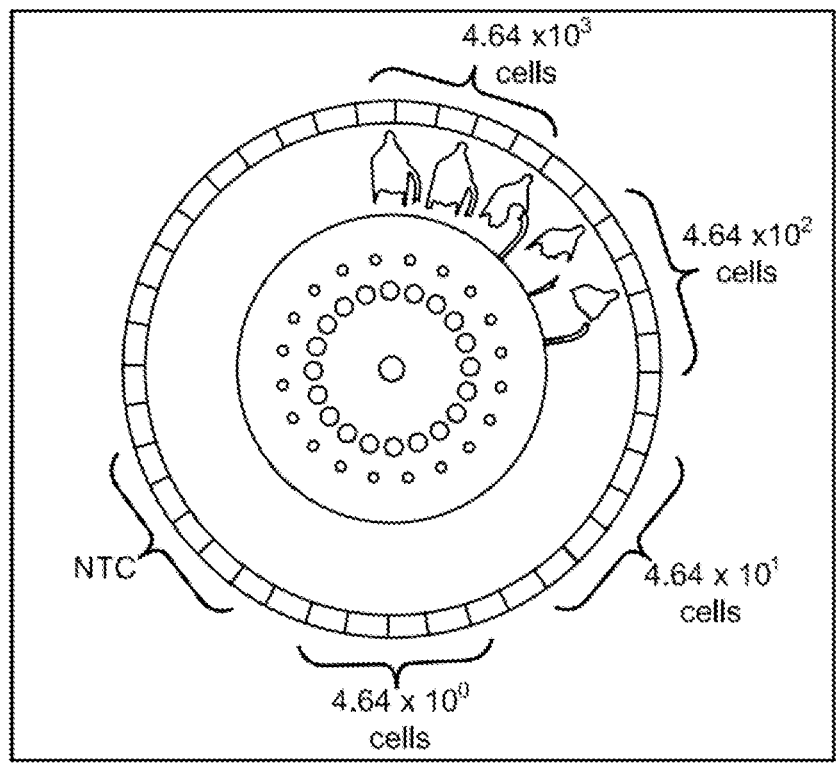

By employing a portable non-contact heating system, a panel of enteric bacteria was detected on-chip by employing LAMP. Successful detection over the range of dilutions was observed (FIG. 11A-11C). Further studies included real-time fluorescence detection of *C. jejuni* amplification via LAMP using a SYTO® 9 dye (FIG. 12A-12C).

Example 6: Simultaneous Protein and Nucleic Acid Detection on a Centrifugal Microfluidic Device Rapid identification of biological agents, such as toxins and pathogens, is critical in situations involving infection or exposure to unknown substances. This demands efficient and comprehensive diagnostic methods. Unfortunately, traditional diagnostic tools are narrowly designed to detect a particular class of biomolecule, typically either proteins or nucleic acids. This is due to the multitude of unique operating conditions and sample preparation techniques required for different assay types.

One key operating condition that differs between protein and nucleic acid detection is temperature. Specifically, nucleic acid tests most often require an elevated temperature for the amplification process. Despite the many multiplexing methods used to expand the range of targets, these methods are still limited to a particular reaction type.

Here is disclosed a method for simultaneously performing both protein and nucleic acid detection modalities for an array of biological samples on a single centrifugal microfluidic device via selective heating using an infrared emitter and specially designed mask. In particular, we can target both proteins and nucleic acids in parallel by combining the high performance rotary and temperature control capabilities of our platform with the strengths of our assay design.

In one non-limiting embodiments, the platform features a servomotor-based rotary control system capable of spinning our microfluidic disc at both slow speeds, to be used during our heating step, and high speeds for centrifugation. Our platform also features a non-contact temperature control system that uses an infrared emitter to uniformly heat the disc for isothermal amplification of nucleic acids via techniques such as LAMP. When combining immunoassays for protein detection with LAMP reactions for nucleic acid detection, an opaque mask can be used to selectively prevent heating of the immunoassay chambers, allowing the two detection schemes to operate side-by-side on a single disc. This functionality can be paired with 1) the sedimentation-based immunoassay designed for our platform, which requires minimal sample preparation and offer high sensitivity and 2) LAMP assays, which are extremely robust and easy to perform. This consolidation of assay types enables an expanded range of detectable targets and provides the opportunity to extract a more complete set of information about a biological sample.

The system can include one or more additional structural features to selectively heat portions of the device. As seen in FIG. 2A, the system 200 can include an infrared emitter 201 and a mask 203 (e.g., an optically opaque mask) configured to include an opening 204. By positioning the opening 204 above a particular assay area 215, that area is selectively heated by the emitter 201. The remaining shielded portions of the disc 210 will not be heated. If the mask 203 is configured to rotate with the disc 210, then selective heating can be maintained during rotation 220 by the motor module 230. The mask 203 can be provided to be in proximity to a first surface (e.g., the top surface) of the disc 210, and the detection module 240 can be provided to be in proximity to a second surface (e.g., the bottom surface) of the disc 210, in which the second surface opposes the first surface. In this way, the mask will not interfere with the detection signal to be detected by the detection module.

Figure 13:
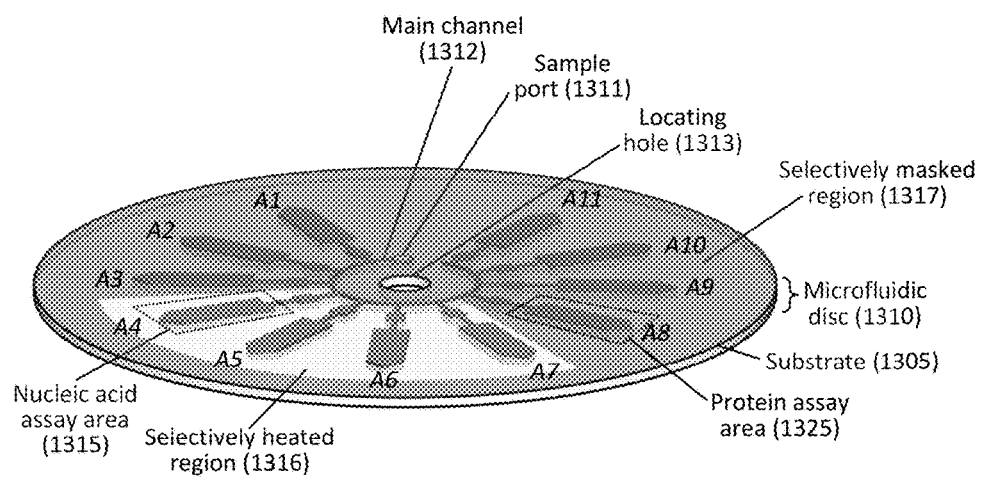
FIG. 13 shows an exemplary disc having a plurality of assay areas labeled A1 to A11 for use with a mask to provide a selectively heated region 1316 and a selectively masked region 1317.

As seen in FIG. 13, the device can be configured to have portions optimized for detecting nucleic acid targets or polypeptide targets. In one instance, the mask can be configured to provide an opening that defines the selectively heated region 1316 of the substrate 1305 and to provide a shielded portion that defines the selectively masked region 1317 of the substrate 1305. Any useful number of assay areas can be exposed within the opening and, thus, be employed as nucleic acid assay areas 1315. As seen in FIG. 13, assay areas A4-A7 are exposed within the opening, thus these areas constitute the selectively heated region 1316. Other assay areas A1-A3, A8-A11 are shielded and will not be heated by the focal point of the emitter. In one instance, shielded areas A8-A11 can be employed as protein assay areas 1325. In another instance, shielded areas A1-A3 can be employed as areas for performing control or baseline measurements.

In one embodiment, the mask can include shielded regions over the main channel 1312 and/or the sample port 1311 to reduce excessive heating of the sample, which can result in fluid leakage, pressure build-up, and/or sample deactivation. The mask can also include an alignment hole that aligns with the locating hole 1313 of the disc 1310, so that the mask and the disc can be aligned together and rotated along a central rotational axis of the motor module.

Figure 14:
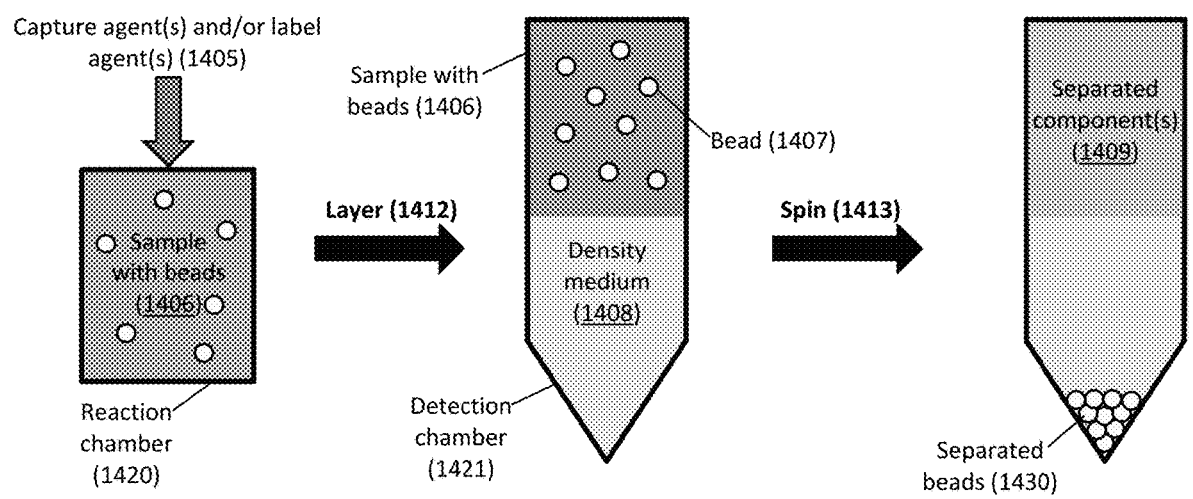
FIG. 14 shows a schematic of an exemplary method of detection by layering 1412 and spinning 1413 the sample.

The system can be employed to conduct any useful assay. FIG. 14 provides an exemplary method, e.g., for performing an assay. The method can include incubating the sample with one or more capture agents and/or one or more label agents. The incubating step can include a single stage of incubation with desired agents or multiple stages of incubation with one or more desired agents at each step. In one non-limiting instance, the incubation step includes incubating with one or more capture agents 1405 (e.g., attached to a bead or provided as a complex with a bead) and then incubating with one or more label agents (e.g., for a time sufficient to allow binding of the detection to the target-bead complex).

After obtaining a sample with particles (e.g., beads), the sample can be introduced to a density medium in any useful manner. Thus, in one instance, the method can include layering 1412 a sample with beads 1406 (e.g., any described herein, including any mixture herein having one or more beads) on a density medium 1408.

Separation can be affected in any useful manner. In one instance, separation can include use of a sedimentation force (e.g., a centrifugal force) to propel particles through the density medium, in which the extent of separation can depend on one or more physical characteristics that affect fluid flow and fluid forces (e.g., such characteristics including particle density, particle size, particle geometry, etc.). In some embodiments, denser components will travel through the density medium, whereas less dense components (e.g., unreacted capture agents, unreacted detection agents, biological components of the sample such as cellular debris, buffer, unreacted agents and reagents, etc.) will remain within a bulk fluid separated from the density medium. In this way, a combination of the beads and the density medium provides effective separation of the targets to be detected. Accordingly, in one non-limiting instance as in FIG. 14, the method can further include spinning 1413 the sample in proximity to the density medium 1408, thereby providing one or more separated components 1409 and separated beads 1430.

The methods herein can be implemented in any useful device (e.g., a microfluidic device). As seen in FIG. 14, the device can include a chamber (e.g., a reaction chamber 1420) configured to store a sample (e.g., a sample with beads 1406). The same chamber can be employed for each step, or a different chamber can be employed for at least one step (e.g., each and every step). When the same chamber is employed, then agents can deliver to that chamber (e.g., by way of one or more channels, vias, valves, etc.). When a different chamber is employed, then the agent can be pre-stored within that chamber and/or delivered to that chamber (e.g., by way of one or more channels, vias, valves, etc.).

As also seen in FIG. 14, the device can include a separate chamber configured to include a density medium, e.g., a detection chamber 1421. The detection chamber can be pre-loaded with a density medium 1408. Alternatively, the density chamber can be configured to receive a density medium, e.g., by way of a channel, valve, via, etc. The geometry and volume of the detection chamber can be configured to promote separation, signal detection, etc. In one non-limiting instance, the detection chamber can be tapered at one end (e.g., located in proximity to a periphery of a microfluidic disc).

Any useful capture and detection methodologies can be employed, e.g., within the method and/or the device. Based on the desired target of interest, the capture agent can be chosen to bind (e.g., selectively and/or specifically bind) the target. For instance, if the target is a protein, then the capture agent can be another protein that binds the protein target. In one embodiment, the target can be an antigen, and the capture agent can be an antibody that binds that antigen. In another embodiment, the target can be an antibody, and the capture agent can be an antigen that binds that antibody. In another instance, the target and capture agent are selected from a reactive pair (e.g., an antibody-antigen pair, a cross-linker reaction pair, a binding reaction pair, or a click-chemistry reaction pair); or a portion of the target and capture agent includes a reactive pair (e.g., an antibody-antigen pair, a cross-linker reaction pair, a binding reaction pair, or a click-chemistry reaction pair). In yet another instance, if the target is a nucleic acid, then the capture agent can be another nucleic acid (e.g., a sufficiently complementary nucleic acid) that hybridizes to the target.

Figure 15A:
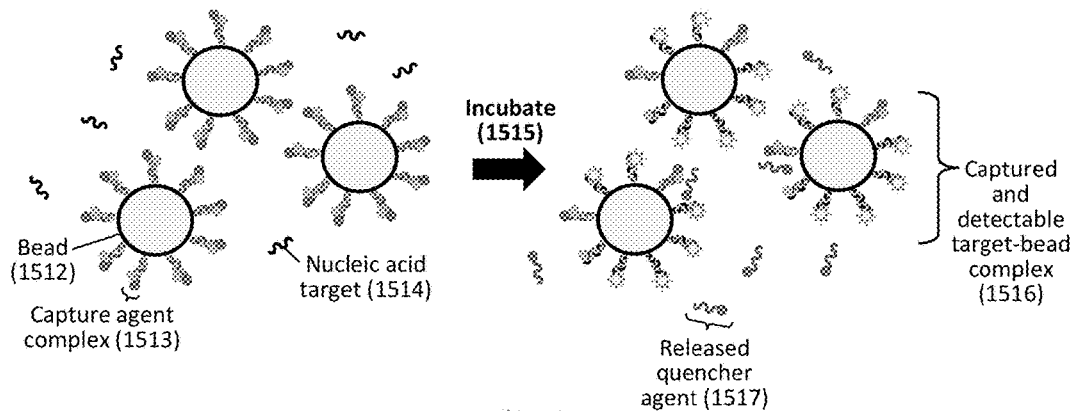
FIG. 15A-15C shows schematics of exemplary methods for detecting a nucleic acid target. Provided are methodologies that employ a capture agent complex 1513 (e.g., a FRET pair) disposed on a surface of a particle (e.g., a bead 1512) (FIG. 15A-15B) and a cationic surface 1522A of a particle (e.g., a bead 1522) to capture an anionic nucleic acid target (FIG. 15C).
Figure 15B:
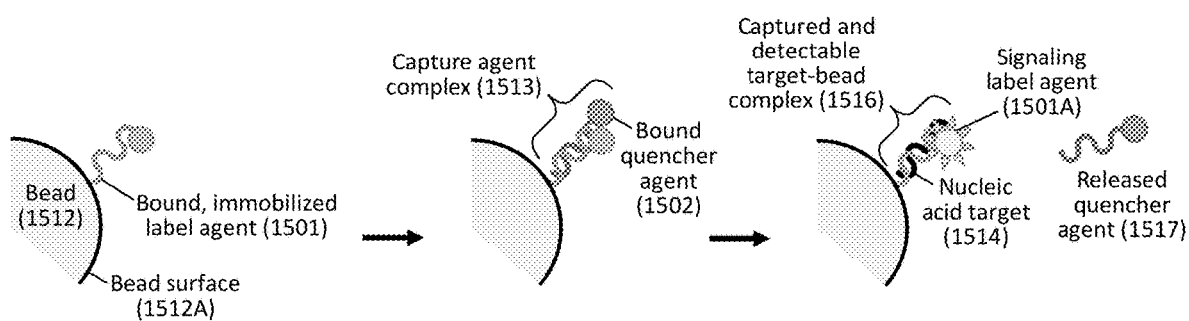

FIG. 15A-15B provides one exemplary capture and detection methodology for a nucleic acid target. As can be seen, the sample can include a target 1514 that is a nucleic acid. To capture this target, beads are employed, in which the bead 1512 includes one or more capture agent complexes 1513 that is a bound immobilized label agent 1501 disposed on a surface 1512A of the bead 1512. The capture agent complex 1513 also includes a bound quencher agent 1502, in which the nucleic acid portion of the quencher agent hybridized with the label agent 1501. Furthermore, the quencher label of the agent 1502 is in proximity to the fluorescent label of the agent 1501, thereby quenching the fluorescence of the fluorescent label by way of Förster resonance energy transfer (FRET).

After incubating 1515 the sample with the bead 1512, captured and detectable target-bead complexes 1516 will be formed if the desired target is present in the sample. Furthermore, the quencher agent will be released 1517, thereby resulting in a detectable signal from the signaling label agent 1501A of the bound immobilized label agent 1501.

Figure 15C:
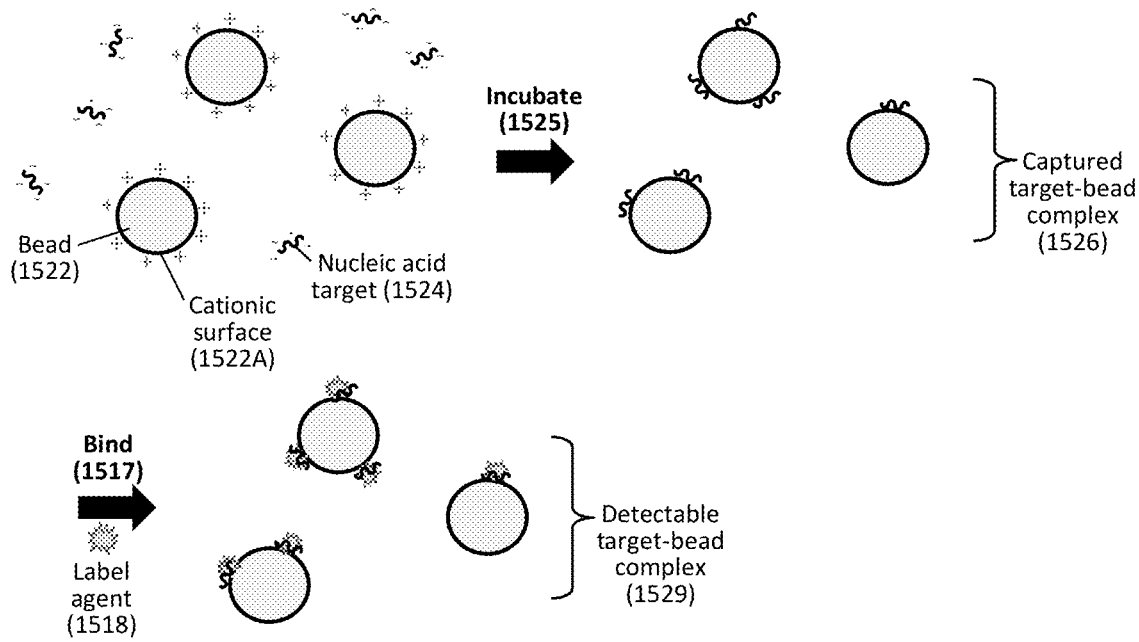

Alternatively, FIG. 15C provides another exemplary capture and detection methodology for a nucleic acid target. Here, the bead 1522 includes a cationic surface 1522A, which can electrostatically interact with anionic targets, such as nucleic acid targets 1524. After incubating 1525 the sample with the bead 1522, captured target-bead complexes 1526 will be formed if the desired target is present in the sample. Detection of the captured complex can include binding 1517 the complex 1526 with a label agent 1518 (e.g., an intercalating dye or another label that interacts with the target) configured to bind the target, thereby resulting in a detectable target-bead complex 1529.

Figure 16A:
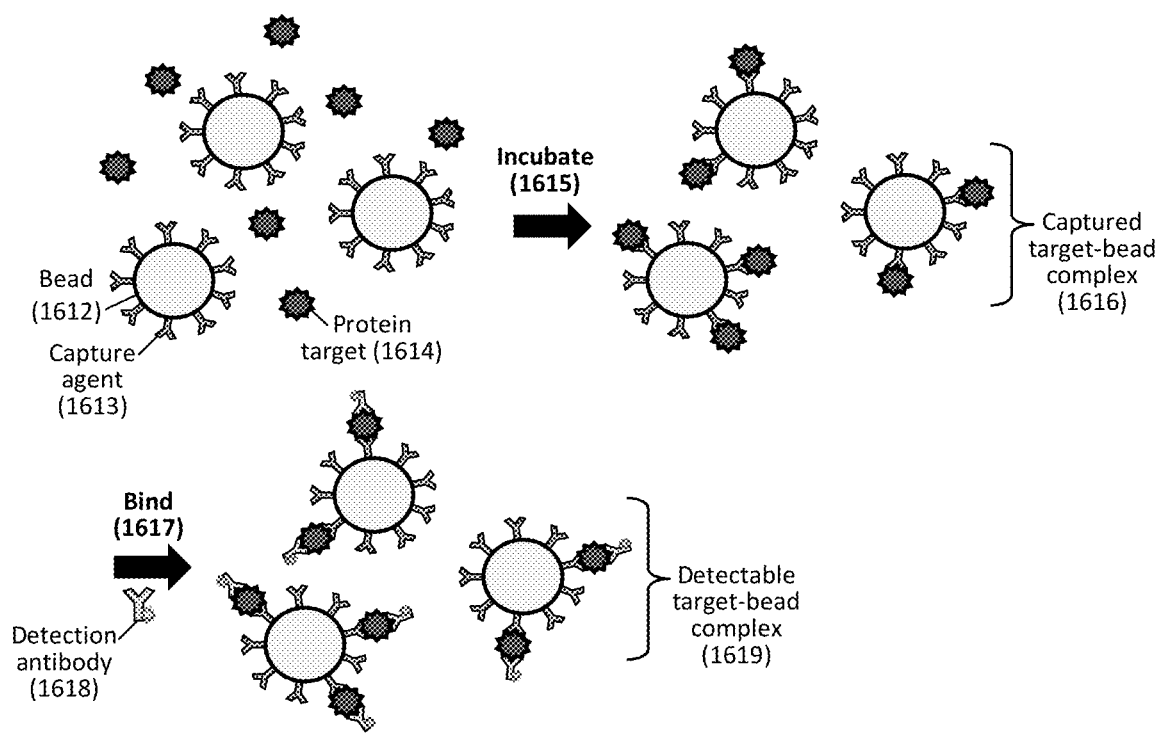
FIG. 16A-16B shows schematics of exemplary methods for detecting a polypeptide target. Provided are methodologies that employ a capture agent 1613 (e.g., an antibody) disposed on a surface of a particle (e.g., a bead 1612) (FIG. 16A) and another capture agent 1623 disposed on a surface of a particle (e.g., a bead 1622) (FIG. 16B).

FIG. 16A provides one exemplary capture and detection methodology for a polypeptide agent. As can be seen, the sample can include a target 1614 that is a protein antigen. To capture this target, beads are employed, in which the bead 1612 includes one or more capture agents 1613 that is a capture antibody disposed on a surface of the bead. The capture antibody can be linked to the bead in any useful manner, e.g., by use of one or more reaction pairs between the antibody and the bead. After incubating 1615 the sample with the bead 1612, captured target-bead complexes 1616 will be formed if the desired target is present in the sample. At times, the target may be present within the sample but bound within a complex, in which case a dissociation agent can be employed to release the target from the complex, thereby allowing the target to bind the capture agent.

Detection of the captured complex can be accomplished in any useful manner (e.g., by use of a primary antibody conjugate as in a direct assay, by use of a secondary antibody conjugate as in an indirect assay or a capture sandwich assay, by use of an enzymatic substrate, etc.). As can be seen in FIG. 16A, detection can include binding 1617 the complex 1616 with a detection antibody 1617 configured to bind the target, thereby resulting in a detectable target-bead complex 1619.

Figure 16B:
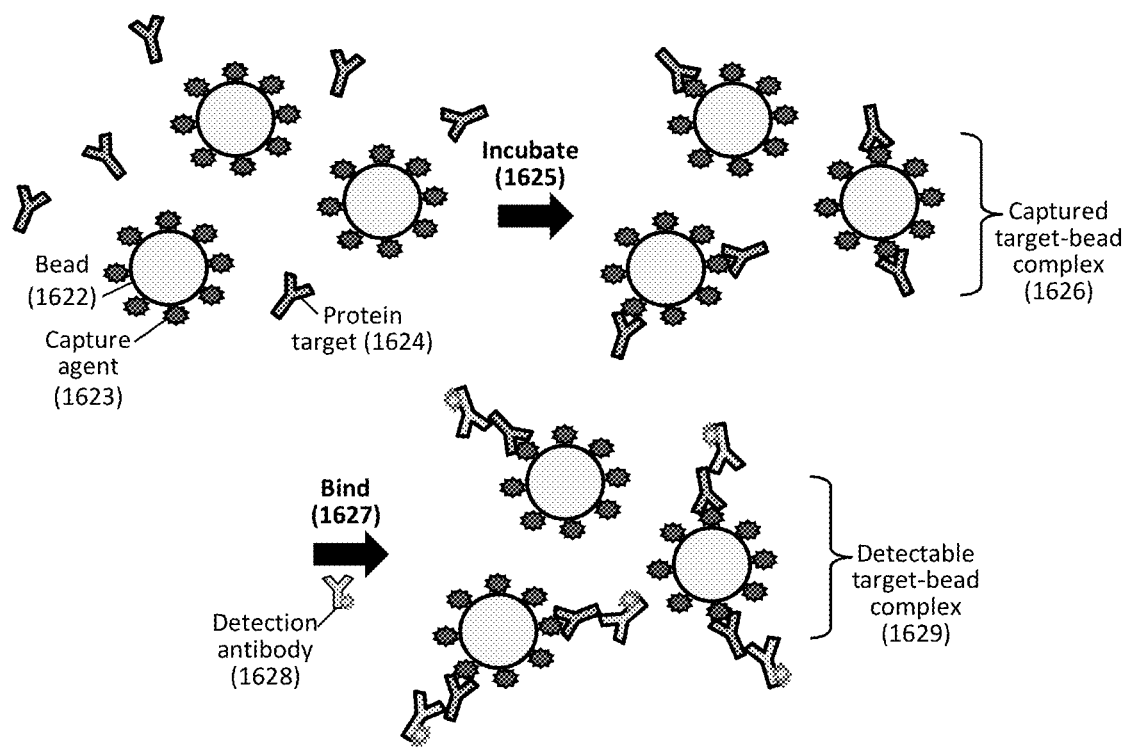

FIG. 16B provides another exemplary capture and detection methodology for a polypeptide target. As can be seen, the sample can include a target 1624 that is a protein antibody. To capture this target, the bead 1622 includes one or more capture agents 1623 that is a capture antigen disposed on a surface of the bead. The capture antigen can be linked to the bead in any useful manner, e.g., by use of one or more reaction pairs between the antigen and the bead. After incubating 1625 the sample with the bead 1622, captured target-bead complexes 1626 will be formed if the desired target is present in the sample. At times, a dissociation agent can be employed. Detection can include binding 1627 the complex 1626 with a detection agent configured to bind the target, thereby resulting in a detectable target-bead complex 1629. In one instance, the detection agent is a detection antibody 1628.

Each bead within a population can have the same capture agent. In some embodiments, each bead has the same surface concentration of capture agents or different surface concentrations can be employed. Furthermore, each population can have the same capture agent or different capture agents. For each capture agent, the same or different detection agent can be employed. In one instance, each detection agent can be associated with a distinguishable detectable signal, such that a distinct signal (e.g., a particular fluorescence signal at a particular emission wavelength) can distinguish one target from another target.

OTHER EMBODIMENTS

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. A method for detecting a nucleic acid target and a polypeptide target in a fluid sample, the method comprising:
    introducing the fluid sample to a system comprising:
        a microfluidic disc comprising a substrate, a first assay area, and a second assay area, in which each of the first and second assay areas is disposed, at least in part, within or on the substrate; and
        a non-contact temperature control system for the microfluidic device, wherein the temperature control system comprising an infrared emitter configured to emit at a wavelength of from about 1 µm to about 5 µm and positioned to direct radiation to a first surface of the microfluidic device, and wherein a focal point of the emitter configured to be positioned on or within the first assay area, or a portion thereof, of the microfluidic device;
    generating a plurality of first complexes on a plurality of first particles in the first assay area, wherein at least one first complex comprises the nucleic acid target and a first label agent;
    generating a plurality of second complexes on a plurality of second particles in the second assay area, wherein at least one second complex comprises the polypeptide target and a second label agent, in which the plurality of first complexes and the plurality of second complexes can be generated sequentially in any order or simultaneously;
    transporting the plurality of first particles through a first density medium in the first assay area and the plurality of second particles through a second density medium in the second assay area; and
    detecting a signal from the first label agent of the first complex bound to the first particle and/or the second label agent of the second complex bound to the second particle.

2. The method of claim 1, wherein the temperature control system further comprises a reflector configured to reflect radiation that is collected from a second surface of the microfluidic device, wherein the second surface opposes the first surface, and wherein the focal point of the emitter and a vertex of the reflector are aligned along a central axis.

3. The method of claim 1, wherein the system further comprises:
    a mask configured to be disposed between the emitter and the microfluidic device, wherein the mask comprises an opening to provide selective heating of the first assay area of the microfluidic device and a shielded region to provide selective masking of the second assay area of the microfluidic device.

4. The method of claim 1, wherein the temperature control system further comprises a cooling fan configured to be in proximity to the emitter.

5. The method of claim 4, wherein the emitter and the cooling fan are configured to be positioned above the microfluidic device, and wherein the reflector and the detection module are configured to be positioned below the microfluidic device.

6. The method of claim 1, wherein the focal point is configured to be positioned on or within the first assay area containing a density medium.

7. The method of claim 6, wherein the first assay area includes a narrowed region and the focal point is configured to be positioned on or within the narrowed region.

8. The method of claim 1, wherein the generating a plurality of first complexes step comprises heating the first assay area with the emitter.

9. The method of claim 1, wherein transporting step comprises spinning the microfluidic disc.

10. The method of claim 1, wherein the detecting step comprises detecting a signal from the first and/or second label agents present in the first and/or second assay area by employing a detection module, and wherein the detection module is configured to generate an electronic detection signal based, at least in part, on the signal from the first and/or second label agents.

11. The method of claim 1, wherein the first density medium has a density lower than a density of the plurality of first particles and higher than a density of the fluid sample within the first assay area.

12. The method of claim 11, wherein the first assay area further comprises a further density medium, a plurality of cells, a plurality of sedimentation particles, and/or a separation layer fluid.

13. The method of claim 1, wherein the second density medium has a density lower than a density of the plurality of second particles and higher than a density of the fluid sample within the second assay area.

14. The method of claim 13, wherein the second assay area further comprises a further density medium, a plurality of cells, a plurality of sedimentation particles, and/or a separation layer fluid.

15. The method of claim 1, wherein the at least one first complex comprises the nucleic acid target hybridized to the first label agent, in which the first label agent is bound to at least one first particle.

16. The method of claim 15, wherein the first label agent comprises a nucleic acid portion configured to hybridize to a sequence of the nucleic acid agent and a detectable label.

17. The method of claim 1, wherein the at least one first complex comprises the nucleic acid target bound to a cationic surface of at least one first particle and wherein the first label agent is bound to the nucleic acid target.

18. The method of claim 1, wherein the at least one second complex comprises the polypeptide target bound to a capture agent disposed on a surface of at least one second particle and wherein the second label agent is bound to the polypeptide target.

19. A method for detecting a nucleic acid target in a fluid sample, the method comprising:
  introducing the fluid sample to a system comprising:
    a microfluidic disc comprising a substrate and a first assay area, which is disposed, at least in part, within or on the substrate; and
    a non-contact temperature control system for the microfluidic device, wherein the temperature control system comprising an infrared emitter configured to emit at a wavelength of from about 1 µm to about 5 µm and positioned to direct radiation to a first surface of the microfluidic device, and wherein a focal point of the emitter configured to be positioned on or within the first assay area, or a portion thereof, of the microfluidic device;
  generating a plurality of first complexes on a plurality of first particles in the first assay area, wherein at least one first complex comprises the nucleic acid target and a first label agent;
  transporting the plurality of first particles through a first density medium in the first assay area; and
  detecting a signal from the first label agent of the first complex bound to the first particle.

20. A method for detecting a nucleic acid target and a polypeptide target in a fluid sample, the method comprising:
  introducing the fluid sample to a system comprising:
    a microfluidic disc comprising a substrate, a first assay area, and a second assay area, in which each of the first and second assay areas is disposed, at least in part, within or on the substrate;
    a non-contact temperature control system for the microfluidic device, wherein the temperature control system comprising an infrared emitter configured to emit at a wavelength of from about 1 µm to about 5 µm and positioned to direct radiation to a first surface of the microfluidic device, and wherein a focal point of the emitter configured to be positioned on or within the first assay area, or a portion thereof, of the microfluidic device; and
    a mask configured to be disposed between the emitter and the microfluidic device, wherein the mask comprises an opening to provide selective heating of the first assay area of the microfluidic device and a shielded region to provide selective masking of the second assay area of the microfluidic device;
  generating a plurality of first complexes on a plurality of first particles in the first assay area, wherein at least one first complex comprises the nucleic acid target and a first label agent, wherein the generating comprises selectively heating the first assay area by employing the mask and the emitter;
  generating a plurality of second complexes on a plurality of second particles in the second assay area, wherein at least one second complex comprises the polypeptide target and a second label agent, in which the plurality of first complexes and the plurality of second complexes can be generated sequentially in any order or simultaneously;
  transporting the plurality of first particles through a first density medium in the first assay area and the plurality of second particles through a second density medium in the second assay area; and
  detecting a signal from the first label agent of the first complex bound to the first particle and/or the second label agent of the second complex bound to the second particle.

* * * * *